(12) United States Patent
Tomatsu

(10) Patent No.: US 12,070,183 B2
(45) Date of Patent: Aug. 27, 2024

(54) MEDICAL OBSERVATION SYSTEM, IMAGE PROCESSING METHOD, AND PROGRAM

(71) Applicant: SONY GROUP CORPORATION, Tokyo (JP)

(72) Inventor: Kei Tomatsu, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 62 days.

(21) Appl. No.: 18/001,597

(22) PCT Filed: Jun. 8, 2021

(86) PCT No.: PCT/JP2021/021664
§ 371 (c)(1),
(2) Date: Dec. 13, 2022

(87) PCT Pub. No.: WO2021/261236
PCT Pub. Date: Dec. 30, 2021

(65) Prior Publication Data
US 2023/0218143 A1    Jul. 13, 2023

(30) Foreign Application Priority Data
Jun. 22, 2020 (JP) ................ 2020-106973

(51) Int. Cl.
*G06T 5/00* (2024.01)
*A61B 1/00* (2006.01)
*G06T 5/80* (2024.01)
*H04N 5/262* (2006.01)

(52) U.S. Cl.
CPC .......... *A61B 1/000095* (2022.02); *G06T 5/00* (2013.01); *G06T 5/80* (2024.01); *H04N 5/2628* (2013.01); *G06T 2207/10068* (2013.01); *G06T 2207/30004* (2013.01)

(58) Field of Classification Search
CPC ........................................ G06T 5/00
See application file for complete search history.

(56) References Cited

FOREIGN PATENT DOCUMENTS

| JP | 10-290777 A | 11/1998 |
| JP | 2000-115753 A | 4/2000 |
| JP | 2012-156672 A | 8/2012 |
| JP | 6150968 B1 | 6/2017 |
| WO | 2019/026929 A1 | 2/2019 |

OTHER PUBLICATIONS

International Search Report and Written Opinion of PCT Application No. PCT/JP2021/021664, issued on Aug. 31, 2021, 09 pages of ISRWO.

*Primary Examiner* — Y Lee
(74) *Attorney, Agent, or Firm* — CHIP LAW GROUP

(57) ABSTRACT

The present disclosure relates to a medical observation system, an image processing method, and a program capable of providing image display more helpful for a surgeon. A correction processing unit performs correction processing on a wide-angle image which is a captured image of a medical treatment target, a clipping processing unit moves a clipping area for a display image clipped from the wide-angle image, and a correction control unit controls the correction processing according to a relative state of the clipping area to the wide-angle image. The present disclosure can be applied to, for example, an endoscopic surgery system.

18 Claims, 23 Drawing Sheets

MEDICAL OBSERVATION SYSTEM, IMAGE PROCESSING METHOD, AND PROGRAM

CROSS REFERENCE TO RELATED APPLICATIONS

This application is a U.S. National Phase of International Patent Application No. PCT/JP2021/021664 filed on Jun. 8, 2021, which claims priority benefit of Japanese Patent Application No. JP 2020-106973 filed in the Japan Patent Office on Jun. 22, 2020. Each of the above-referenced applications is hereby incorporated herein by reference in its entirety.

TECHNICAL FIELD

The present disclosure relates to a medical observation system, an image processing method, and a program, and more particularly to a medical observation system, an image processing method, and a program capable of providing image display more helpful for a surgeon.

BACKGROUND ART

Conventionally, as disclosed in PTL 1, for example, an endoscope is provided with a wide-angle lens at its distal end to ensure a viewing angle.

In a wide-angle image, the closer to its edges, the more distorted. Accordingly, in general, an image clipped from a distortion-corrected wide-angle image is displayed as a display image on a display or the like.

CITATION LIST

Patent Literature

[PTL 1]
JP H10-290777 A

SUMMARY

Technical Problem

However, for a surgeon who performs a surgery while observing a display image which is a clip image rather than the entire wide-angle image, it is not easy to recognize the position of a clipping area for clipping the display image in the entire wide-angle image.

The present disclosure has been made in view of such a situation and provides image more display helpful for a surgeon.

Solution to Problem

A medical observation system according to the present disclosure is a medical observation system that includes: a correction processing unit that performs correction processing on a wide-angle image which is a captured image of a medical treatment target; a clipping processing unit that moves a clipping area for a display image clipped from the wide-angle image; and a correction control unit that controls the correction processing according to a relative state of the clipping area to the wide-angle image.

An image processing method according to the present disclosure is an image processing method performed by a medical observation system includes: performing correction processing on a wide-angle image which is a captured image of a medical treatment target; moving a clipping area for a display image clipped from the wide-angle image; and controlling the correction processing according to a relative state of the clipping area to the wide-angle image.

A program according to the present disclosure is a program that causes a computer to execute: performing correction processing on a wide-angle image which is a captured image of a medical treatment target; moving a clipping area for a display image clipped from the wide-angle image; and controlling the correction processing according to a relative state of the clipping area to the wide-angle image.

In the present disclosure, correction processing is performed on a wide-angle image which is a captured image of a medical treatment target, a clipping area for a display image clipped from the wide-angle image is moved, and the correction processing is controlled according to a relative state of the clipping area to the wide-angle image.

Figure 1:
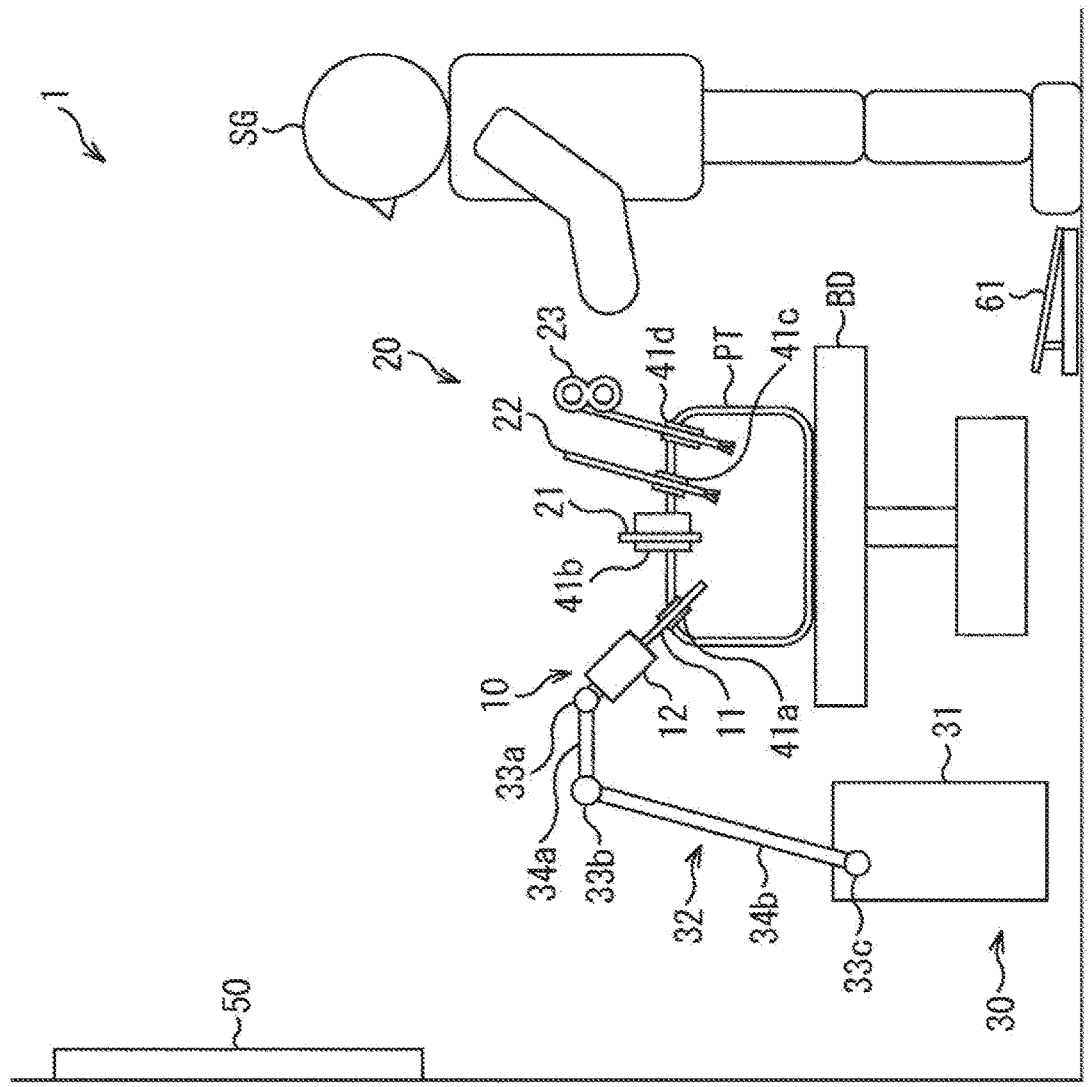
FIG. 1 is a schematic diagram of an endoscopic surgery system to which the technique according to the present disclosure is applied.

Hereinafter, modes for carrying out the present disclosure (hereinafter referred as embodiments) will be described. Here, description will proceed in the following order.

1. Example to which technique according to present disclosure is applicable
2. Configuration example and basic operation of medical observation system
3. First embodiment (correction control 1 according to moving state of clipping area)
4. Second embodiment (correction control 2 according to moving state of clipping area)
5. Third embodiment (display control 1 according to position of clipping area)
6. Fourth embodiment (display control 2 according to position of clipping area)
7. Another configuration example of medical observation system
8. Fifth Embodiment (display control 3 according to position of clipping area)
9. Sixth Embodiment (display control 4 according to position of clipping area)
10. Hardware configuration <1. Example to Which Technique According to Present Disclosure is Applicable>

The technique according to the present disclosure is applied to a medical observation system that can move a clipping area for a display image clipped from a wide-angle image.

(Endoscopic Surgery System)

FIG. 1 is a schematic diagram of an endoscopic surgery system 1 to which the technique according to the present disclosure is applied.

FIG. 1 illustrates a state where a surgeon (doctor) SG is performing a surgery on a patient PT on a patient bed BD.

As illustrated in FIG. 1, the endoscopic surgery system 1 includes an endoscope 10, other surgical instruments 20, and a support arm device 30 for supporting the endoscope 10. Although not illustrated, the endoscopic surgery system 1 includes various types of devices for endoscopic surgery.

In the endoscopic surgery, a plurality of tubular laparotomy instruments called trocars 41a to 41d are punctured into an abdominal wall, instead of cutting the abdominal wall to open an abdomen. Then, a lens barrel 11 of the endoscope 10 and the other surgical instruments 20 are inserted into the body cavity of the patient PT from the trocars 41a to 41d. In the example of FIG. 1, as the other surgical instruments 20, a pneumoperitoneum tube 21, an energy treatment instrument 22 for incising or exfoliating tissues by high-frequency current or ultrasonic vibration and sealing a blood vessel, and forceps 23 are inserted into the body cavity of the patient PT. However, the illustrated surgical instruments 20 are merely exemplary, and as the surgical instruments 20, various types of surgical instruments generally used in an endoscopic surgery such as a tweezer and a retractor may be used.

An image of a surgical site within the body cavity of the patient PT captured by the endoscope 10 is displayed on a display device 50. The surgeon SG performs treatment such as cutting-out of an affected part, using the energy treatment instrument 22 or the forceps 23 while viewing the image of the surgical site displayed on the display device 50 in real time. Although not illustrated, the pneumoperitoneum tube 21, the energy treatment instrument 22, and the forceps 23 are supported by the surgeon SG or an assistant during surgery.

The support arm device 30 includes an arm portion 32 extending from a base portion 31. In the example of FIG. 1, the arm portion 32 includes joint portions 33a, 33b, and 33c and links 34a and 34b, and is driven under the control of a control device (not illustrated). The endoscope 10 is supported by the arm portion 32, and the position and orientation thereof are controlled. This enables the stable fixation of the endoscope 10 in place.

The endoscope 10 includes the lens barrel 11 of which a portion having a predetermined length from its distal end is inserted into a body cavity of the patient PT, and a camera head 12 connected to a base end of the lens barrel 11. Although the endoscope 10 configured as a so-called rigid endoscope having the rigid lens barrel 11 is illustrated in the example of FIG. 1, the endoscope 10 may be configured as a so-called flexible endoscope having a flexible lens barrel 11.

The distal end of the lens barrel 11 is provided with an opening into which a wide-angle lens serving as an objective lens is fitted. A light source device (not illustrated) is connected to the endoscope 10, and light generated by the light source device is guided to the distal end of the lens barrel 11 by a light guide extending inside the lens barrel 11 to irradiate an observation target in the body cavity of the patient PT via the wide-angle lens. The endoscope 10 may be a direct-viewing endoscope or may be a perspective-viewing endoscope or a side-viewing endoscope.

An optical system and an imaging element are provided inside the camera head 12 and light (observation light) reflected from the observation target is focused on the imaging element by the optical system. The observation light is photoelectrically converted by the imaging element, and an electrical signal corresponding to the observation light, that is, an image signal corresponding to an observation image is generated. The image signal is transmitted as RAW data to a camera control unit (CCU) (not illustrated). The camera head 12 has a function of adjusting the magnification and focal length by driving the optical system as appropriate.

For example, in order to cope with stereoscopic vision (3D display) and the like, the camera head 12 may be provided with a plurality of imaging elements. In this case, a plurality of relay optical systems are provided inside the lens barrel 11 in order to guide the observation light to each of the plurality of imaging elements.

Although not illustrated, the endoscopic surgery system 1 is provided with an input device which is an input interface for the endoscopic surgery system 1. The input device includes, for example, a mouse, a keyboard, a touch panel, a switch, a foot switch 61, a lever, and/or the like. In a case in which the input device is configured as a touch panel, the touch panel may be provided on a display surface of the display device 50.

The input device may include a device worn by the surgeon, such as a glasses-type wearable device or a head mounted display (HMD), a camera that can detect the movement of the surgeon, and the like, to be able to receive various types of inputs according to a gesture or line of sight of the surgeon.

With such a configuration, the surgeon SG can perform various treatments while viewing the display image of the surgical site displayed on the display device 50.

(Microscopic Surgery System)

Figure 2:
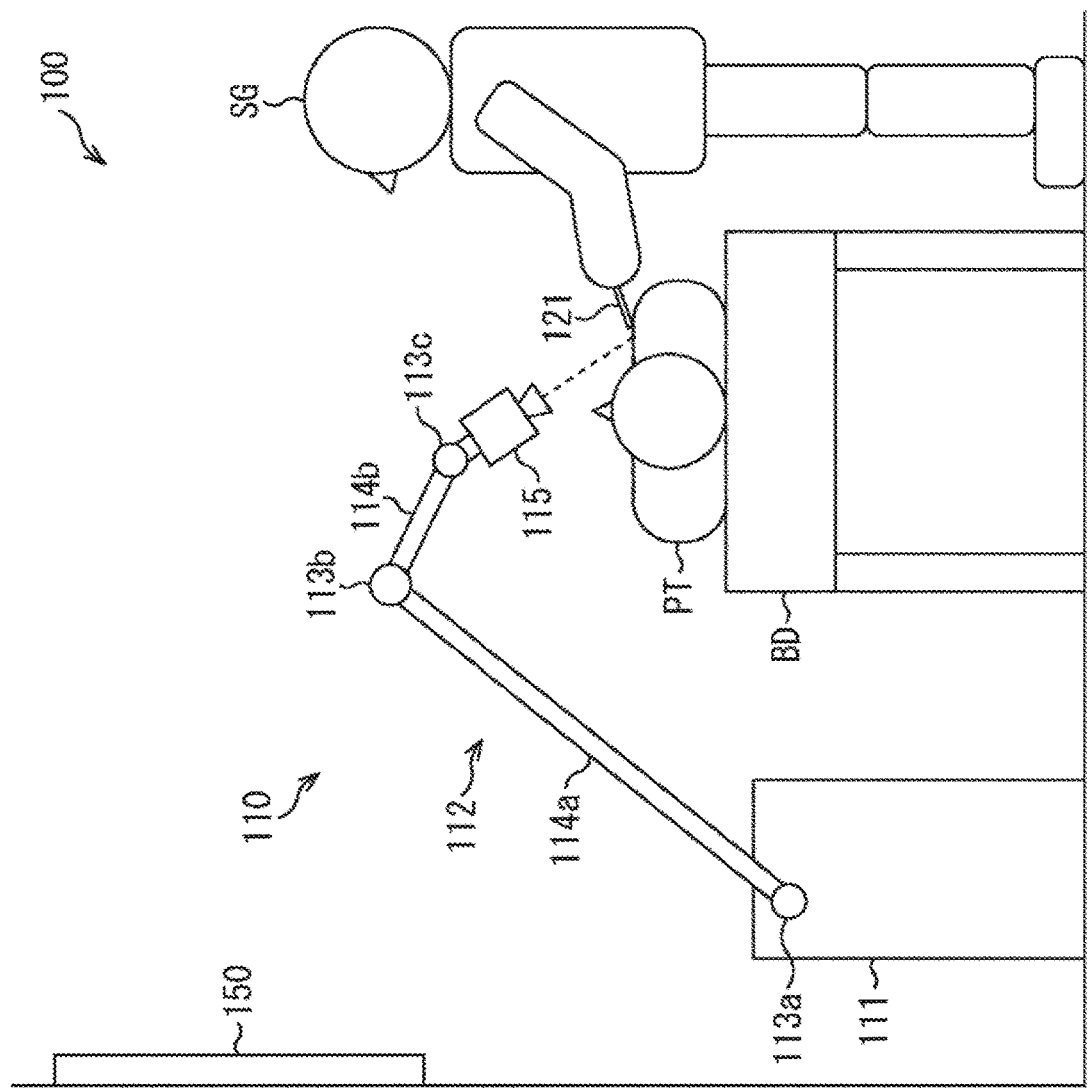
FIG. 2 is a schematic diagram of a microscopic surgery system to which the technique according to the present disclosure is applied.

FIG. 2 is a schematic diagram of a microscopic surgery system 100 to which the technique according to the present disclosure is applied.

FIG. 2 illustrates a state where a surgeon SG is using surgical instruments 121 such as a scalpel, tweezers, and forceps to perform a surgery on a patient PT on a patient bed BD.

A surgical video microscope device 110 is installed beside the patient bed BD.

The surgical video microscope device 110 includes a base portion 111 serving as a base, an arm portion 112 extending from the base portion 111, and an imaging unit 115 connected to the distal end of the arm portion 112. The surgical video microscope device 110 may be an exoscope.

The arm portion 112 has a plurality of joint portions 113*a*, 113*b*, and 113*c*, a plurality of links 114*a* and 114*b* connected by the joint portions 113*a* and 113*b*, and the imaging unit 115 attached to the distal end of the arm portion 112.

In the example of FIG. 2, for simplicity, the arm portion 112 has three joint portions 113*a* to 113*c* and two links 114*a* and 114*b*. In practice, the numbers and shapes of the joint portions 113*a* to 113*c* and the links 114*a* and 114*b*, the directions of the drive axes of the joint portions 113*a* to 113*c*, and the like may be set as appropriate so as to achieve a desired degree of freedom in consideration of the degree of freedom of the position and orientation of the imaging unit 115.

The joint portions 113*a* to 113*c* have a function of rotatably connecting the links 114*a* and 114*b*, and the drive of the arm portion 112 is controlled by driving the rotation of the joint portions 113*a* to 113*c*.

The imaging unit 115 is a unit that includes an optical system for acquiring an optical image of a subject to acquire an image of an imaging target, and is configured as a microscope equipped with a camera capable of capturing moving images and still images, for example. A wide-angle lens is applied as the optical system in an embodiment of the present disclosure. As illustrated in FIG. 2, the orientation and position of the imaging unit 115 are controlled by the surgical video microscope device 110 so that the imaging unit 115 attached to the distal end of the arm portion 112 can capture the state of a surgical site of the patient PT. The imaging unit 115 may be configured to be detachable from the arm portion 112.

A display device 150 is installed at a position facing the surgeon SG. The image of the surgical site acquired by the imaging unit 115 is displayed on the display device 150 after being subjected to various types of image processing by an image processing device built in or external to the surgical video microscope device 110, for example.

With such a configuration, the surgeon SG can perform various treatments while viewing the display image of the surgical site displayed on the display device 150.

<2. Configuration Example and Basic Operation of Medical Observation System>

Next, a configuration example and basic operation of a medical observation system applicable to the endoscopic surgery system 1 or the microscopic surgery system 100 described above will be described.

(Configuration Example of Medical Observation System)

Figure 3:
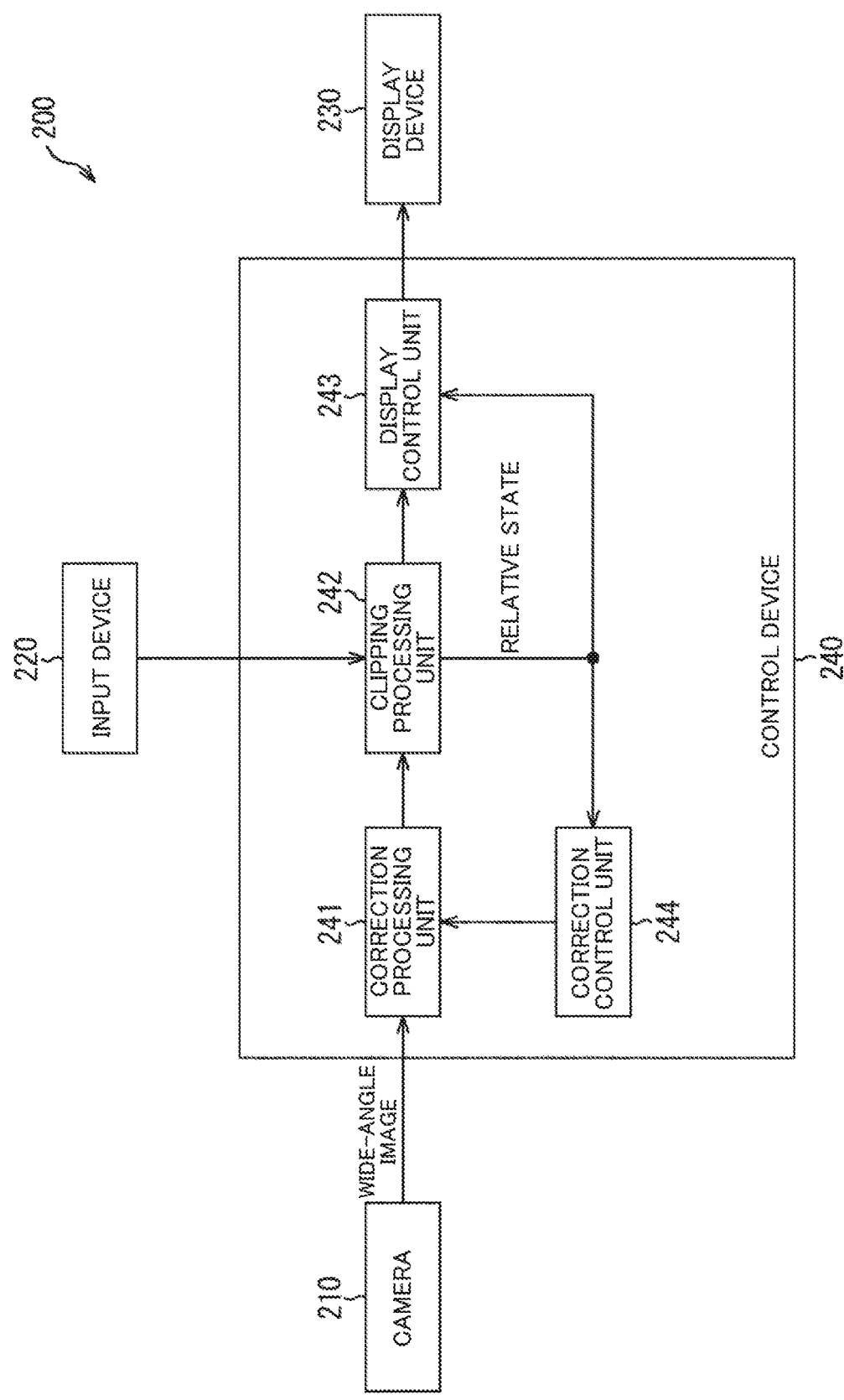
FIG. 3 is a block diagram illustrating a configuration example of a medical observation system according to an embodiment of the present disclosure.

FIG. 3 is a block diagram illustrating a configuration example of a medical observation system according to an embodiment of the present disclosure.

The medical observation system 200 illustrated in FIG. 3 includes a camera 210, an input device 220, a display device 230, and a control device 240.

The camera 210 corresponds to the endoscope 10 (camera head 12) of the endoscopic surgery system 1 or the microscope (imaging unit 115) of the microscopic surgery system 100, and includes an optical system and an imaging element. A wide-angle lens is applied as the optical system included in the camera 210. Specifically, the camera 210 acquires a wide-angle image of a medical treatment target and supplies the wide-angle image to the control device 240. The wide-angle image is a moving image of a surgical site captured in real time, but may be a still image. As the wide-angle lens, an ultra wide-angle lens capable of obtaining an angle of view of 135 degrees or 140 degrees, for example, is used, but a fish-eye lens capable of obtaining a larger angle of view, for example, an angle of view of nearly 180 degrees may be applied. As the wide-angle lens, a wide-angle lens capable of obtaining an angle of view of about 60 degrees to 100 degrees may be applied.

The input device 220 includes an operation device such as a button, a switch, a mouse, a joystick, and a touch panel, and a voice input device such as a microphone, and supplies an operation signal indicating an operation from a user of the medical observation system 200, specifically, a surgeon, to the control device 240.

The display device 230 is configured as a monitor for displaying an image output from the control device 240. The image displayed on the display device 230 is observed by the user (surgeon).

The control device 240 is configured as an image processing device to which the technique according to the present disclosure is applied, and is configured as, for example, a camera control unit (CCU) including a central processing unit (CPU), a graphics processing unit (GPU), and the like.

The control device 240 generally controls the image capturing with the camera 210 and the display with the display device 230 based on the operation signal from the input device 220. For example, the control device 240 clips a part of a wide-angle image obtained from the camera 210 and outputs the clip image as a display image to the display device 230.

The control device 240 includes a correction processing unit 241, a clipping processing unit 242, a display control unit 243, and a correction control unit 244.

The correction processing unit 241 performs correction processing on the wide-angle image obtained from the camera 210. Specifically, the correction processing unit 241 performs distortion correction on the distorted wide-angle image to generate a corrected wide-angle image with no distortion, and supplies the corrected wide-angle image to the clipping processing unit 242.

In a wide-angle image as known, the closer to its edges, the darker, that is, the less the amount of light. In this viewpoint, the correction processing unit 241 may perform luminance correction on the wide-angle image to generate a corrected wide-angle image with constant brightness.

The correction processing unit 241 may also supply the wide-angle image on which the correction processing has not been performed as it is to the clipping processing unit 242 under the control of the correction control unit 244, which will be described later.

The clipping processing unit 242 clips a part of the wide-angle image obtained from the correction processing unit 241 and supplies the clip image as a display image to the display control unit 243. A clipping area for clipping the display image from the wide-angle image moves on the wide-angle image based on detection of a trigger for moving the clipping area. For example, the clipping area moves in real time on the wide-angle image based on an operation signal indicating a user operation through the input device 220. For example, in a case where the image of a surgical instrument in the wide-angle image is recognized, and the clipping area is moved so as to follow the movement of the surgical instrument whose image has been recognized, the clipping area moves on the wide-angle image in real time based on a detection signal indicating that the movement of the surgical instrument to be followed has been detected.

The clipping processing unit 242 also supplies to the display control unit 243 and the correction control unit 244 relative state information indicating a relative state of the clipping area to the wide-angle image. This relative state includes at least one of the moving state of the clipping area in the wide-angle image (at least one of presence or absence of movement, moving speed, moving direction, etc.) and the position of the clipping area in the wide-angle image.

The display control unit 243 causes the display device 230 to display the display image obtained from the clipping processing unit 242 by controlling the display device 230. The display control unit 243 can also control the display of the display image according to the relative state of the clipping area to the wide-angle image, which is indicated by the relative state information obtained from the clipping processing unit 242.

The correction control unit 244 controls the correction processing of the correction processing unit 241 according to the relative state of the clipping area to the wide-angle image, which is indicated by the relative state information obtained from the clipping processing unit 242.

Details of the control of the correction processing will be described in an embodiment described later. In brief, when the relative state of the clipping area changes, the correction control unit 244 disables the correction processing or adjusts the correction amount for the correction processing according to changes in the relative state. When the relative state of the clipping area is constant with no change, the correction control unit 244 enables the correction processing.

(Basic Operation of Medical Observation System)

Next, a flow of basic operation of the medical observation system 200 will be described with reference to the flowchart of FIG. 4.

Figure 4:
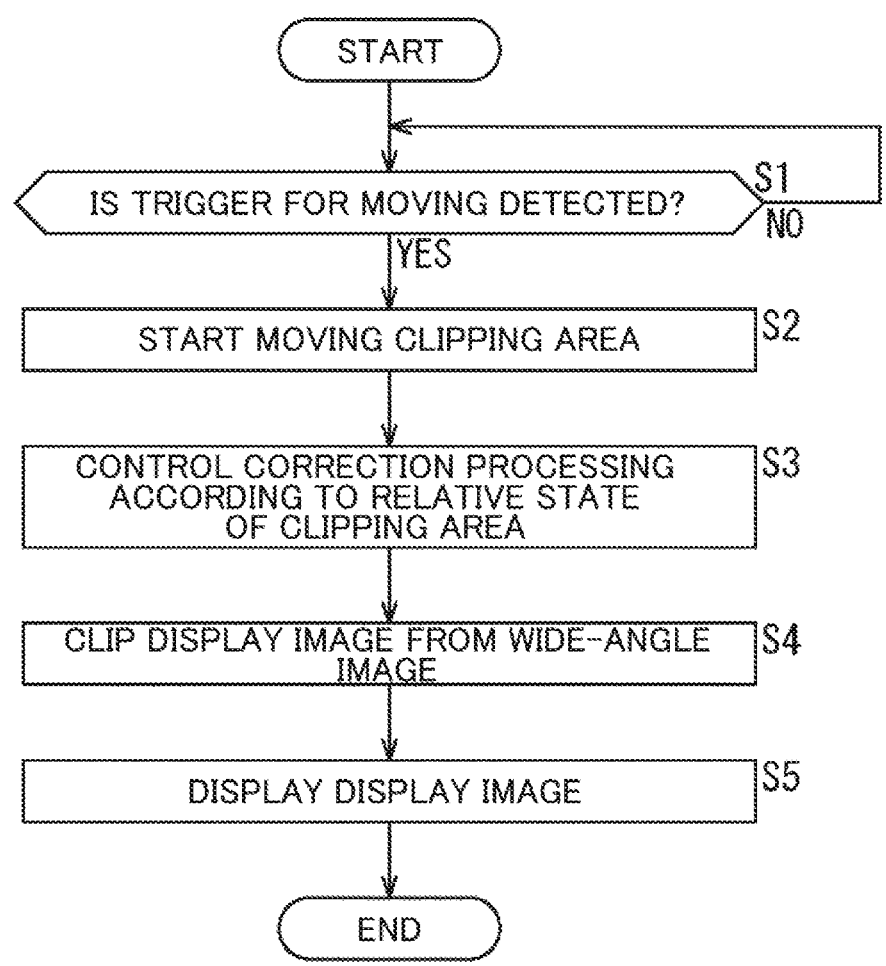
FIG. 4 is a flowchart illustrating a flow of basic operation of the medical observation system.

The processing of FIG. 4 is started, for example, with the relative state of a clipping area to a wide-angle image being constant, that is, with the correction processing being performed on the wide-angle image from the camera 210 and then a display image clipped from the corrected wide-angle image being displayed on the display device 230.

In step S1, the clipping processing unit 242 of the control device 240 determines whether or not a trigger for moving the clipping area has been detected. For example, step S1 is repeated until a user operation to move the clipping area is received, and when the operation to move the clipping area is received, the processing proceeds to step S2.

The user operation to move the clipping area may be received based on a speech voice to instruct the movement of the clipping area, or may be received through an operation device such as a joystick. The user operation to move the clipping area may be received based on the result of detecting the line of sight of the user. As described above, in step S1, the movement of a surgical instrument to be followed in the wide-angle image may be detected and then the processing may proceed to step S2.

In step S2, the clipping processing unit 242 of the control device 240 starts moving the clipping area based on the user operation to move the clipping area. This will change the relative state of the clipping area to the wide-angle image.

Accordingly, in step S3, the correction control unit 244 of the control device 240 controls the correction processing of the correction processing unit 241 according to the relative state of the clipping area to the wide-angle image.

Specifically, when the relative state of the clipping area changes, the correction control unit 244 disables the correction processing or adjusts the correction amount for the correction processing according to changes in the relative state. When the relative state of the clipping area does not change, the correction control unit 244 enables the correction processing.

In step S4, the clipping processing unit 242 of the control device 240 clips a display image from the wide-angle image on which the correction processing has been performed by the correction processing unit 241 or from the original wide-angle image.

In step S5, the display control unit 243 of the control device 240 causes the display device 230 to display the display image clipped from the wide-angle image.

As described above, when the relative state of the clipping area to the wide-angle image is changed, at least a display image is clipped from the wide-angle image on which the correction processing has not been fully performed.

In situations where it is not possible to recognize the position of the clipping area in the entire wide-angle image, even if the clipping area is at an edge of the wide-angle image, the surgeon cannot recognize that the clipping area is prevented from moving any further, resulting in a risk that the progress of the surgery would be hindered.

In contrast, according to the above-described processing, when the clipping area is at an edge of the wide-angle image by the surgeon moving the clipping area, the distortion or darkness of the display image makes it possible for the surgeon to recognize that the clipping area is prevented from moving any further. As a result, it is possible to provide image display more helpful for the surgeon.

A specific embodiment of correction control according to the relative state of the clipping area to the wide-angle image will be described below. In the embodiments described below, it is assumed that distortion correction is performed on the wide-angle image by the correction processing unit 241. However, luminance correction may be performed on it as described above.

<3. First Embodiment (Correction Control 1 According to Moving State of Clipping Area)>

Figure 5:
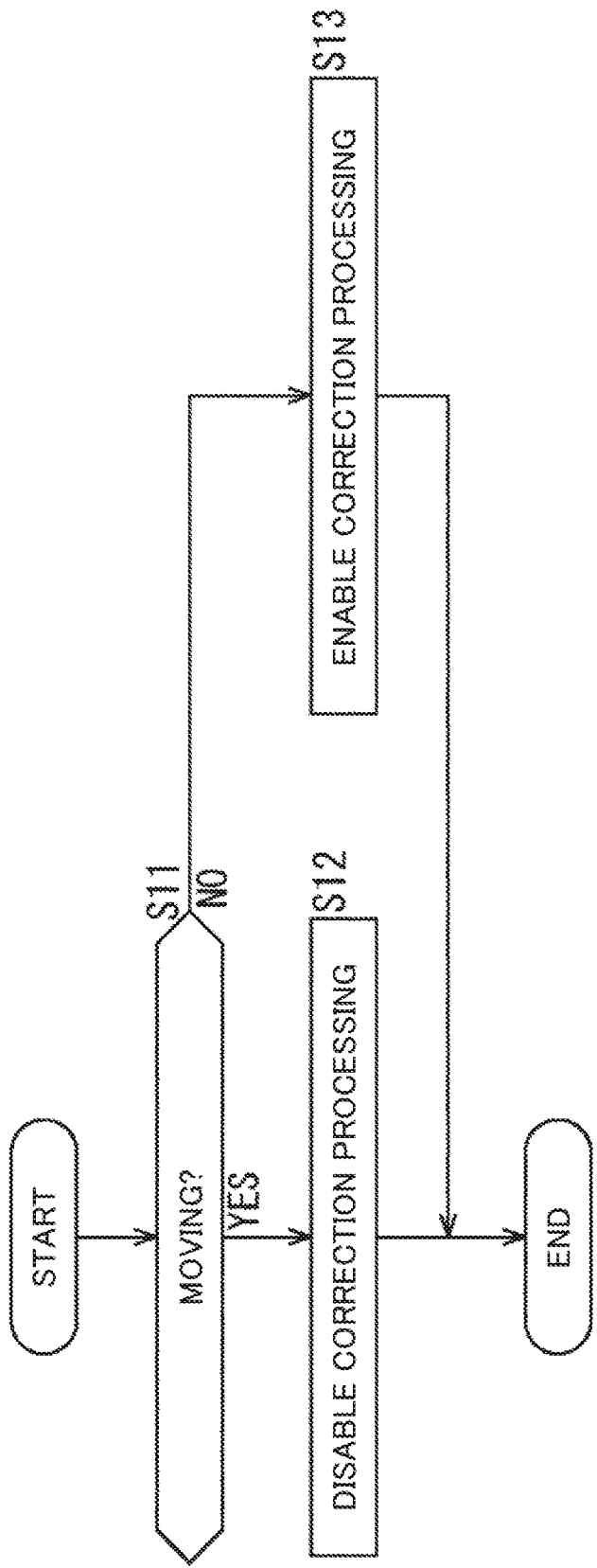
FIG. 5 is a flowchart illustrating a flow of operation of a correction control unit, according to the first embodiment.

FIG. 5 is a flowchart illustrating a flow of operation of the correction control unit 244, according to a first embodiment. The correction control unit 244 of the present embodiment disables or enables the correction processing of the correction processing unit 241 according to whether a clipping area is moving or stopped in a wide-angle image.

In step S11, the correction control unit 244 determines whether or not the clipping area is moving.

If it is determined in step S11 that the clipping area is moving, the processing proceeds to step S12, and then the correction control unit 244 disables the correction processing of the correction processing unit 241.

On the other hand, if it is determined in step S11 that the clipping area is not moving, that is, if the clipping area is stopped, the processing proceeds to step S13, and then the correction control unit 244 enables the correction processing of the correction processing unit 241.

Clipping of a display image according to the present embodiment will now be described with reference to FIGS. 6 and 7. For ease of explanation, the subject of a wide-angle image is assumed to be a chessboard pattern in which it is easy to recognize a distorted image, and the same applies to the following embodiments.

Figure 6:
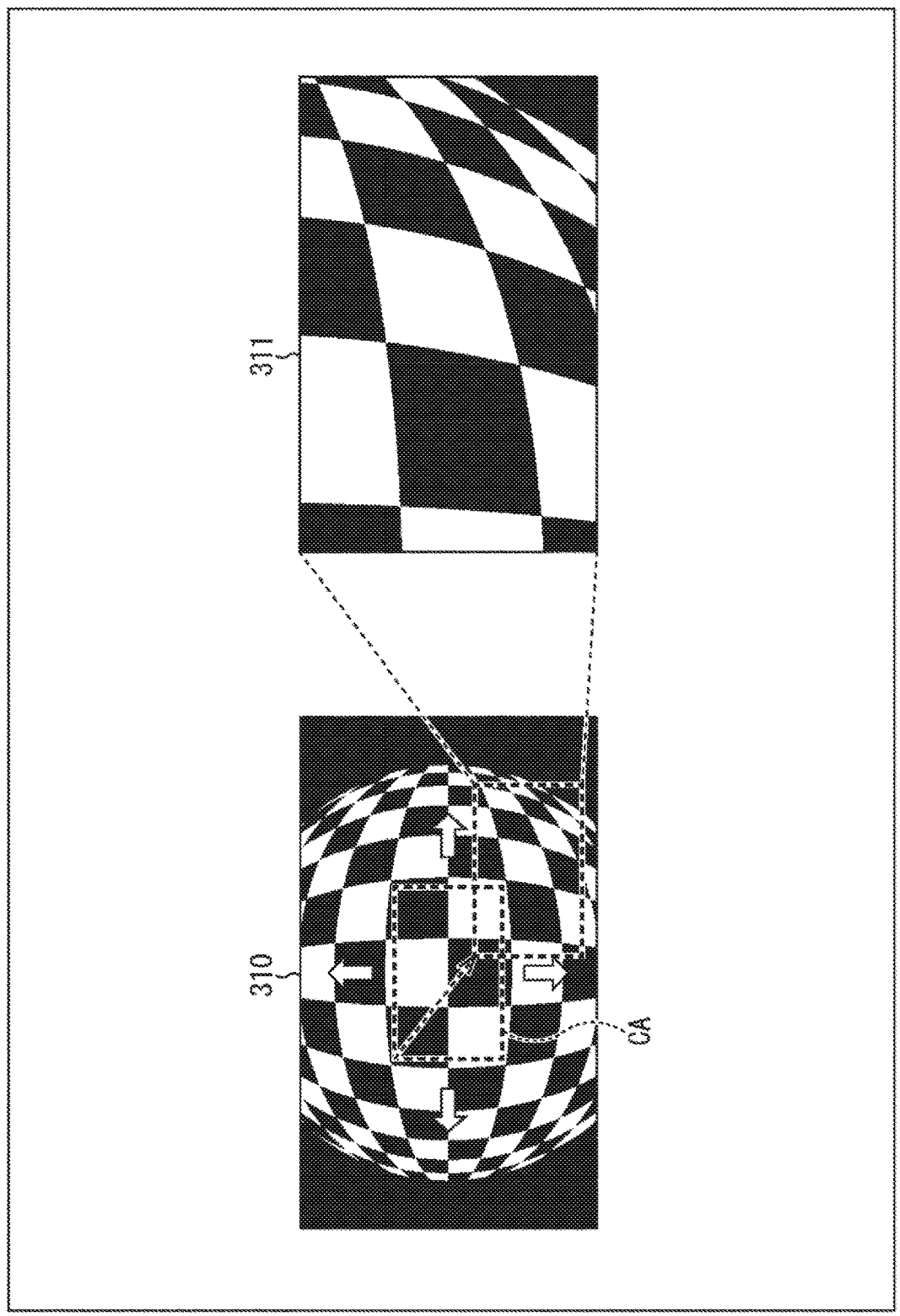
FIG. 6 is a diagram illustrating an example of clipping a display image.

As illustrated in FIG. 6, in a case where a clipping area CA is located in the center of a wide-angle image 310, the clipping area CA is movable up, down, left, and right. From this state, when the clipping area CA is moved to the lower right based on a user operation to move the clipping area CA, a display image 311 corresponding to the clipping area CA is clipped from the wide-angle image 310 as it is without having not been subjected to the correction processing (distortion correction).

Figure 7:
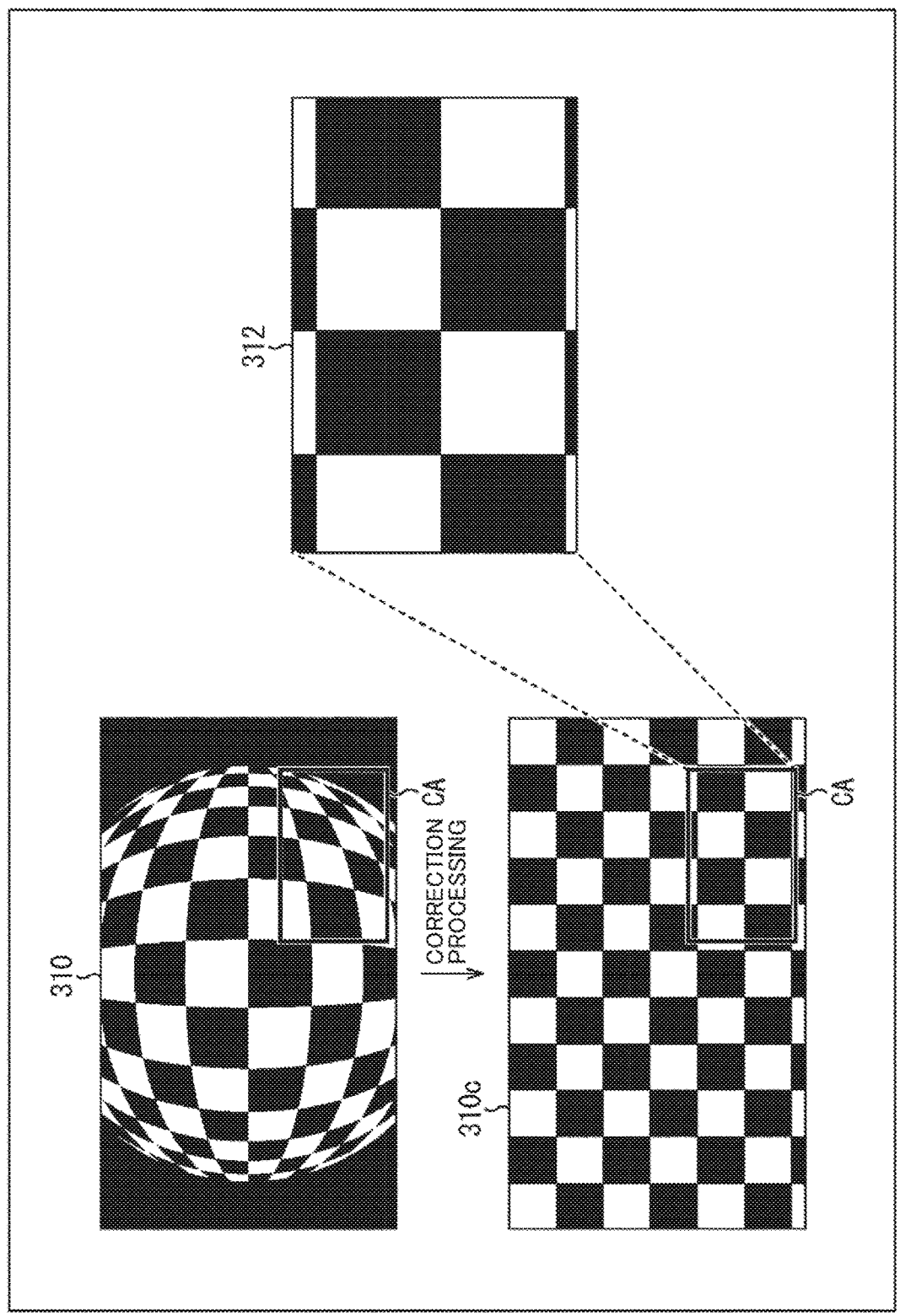
FIG. 7 is a diagram illustrating an example of clipping a display image.

On the other hand, as illustrated in FIG. 7, in a case where the clipping area CA is stopped at the lower right of the wide-angle image 310, a display image 312 corresponding to the clipping area CA is clipped from a corrected wide-angle image 310*c* in which the correction processing (distortion correction) has been performed on the wide-angle image 310.

According to the above-described processing, when the surgeon moves the clipping area, the closer to an edge of the wide-angle image the clipping area is, the more the display image is distorted, so that it is possible to easily recognize that the clipping area is approaching an edge of the wide-angle image. When the surgeon stops the clipping area, even if the clipping area is located near an edge of the wide-angle image, a display image with no distortion is displayed, so that the surgery can proceed smoothly.

As described above, according to the present embodiment, it is possible to provide image display more helpful for the surgeon.

<4. Second Embodiment (Correction Control 2 According to Moving State of Clipping Area)>

Figure 8:
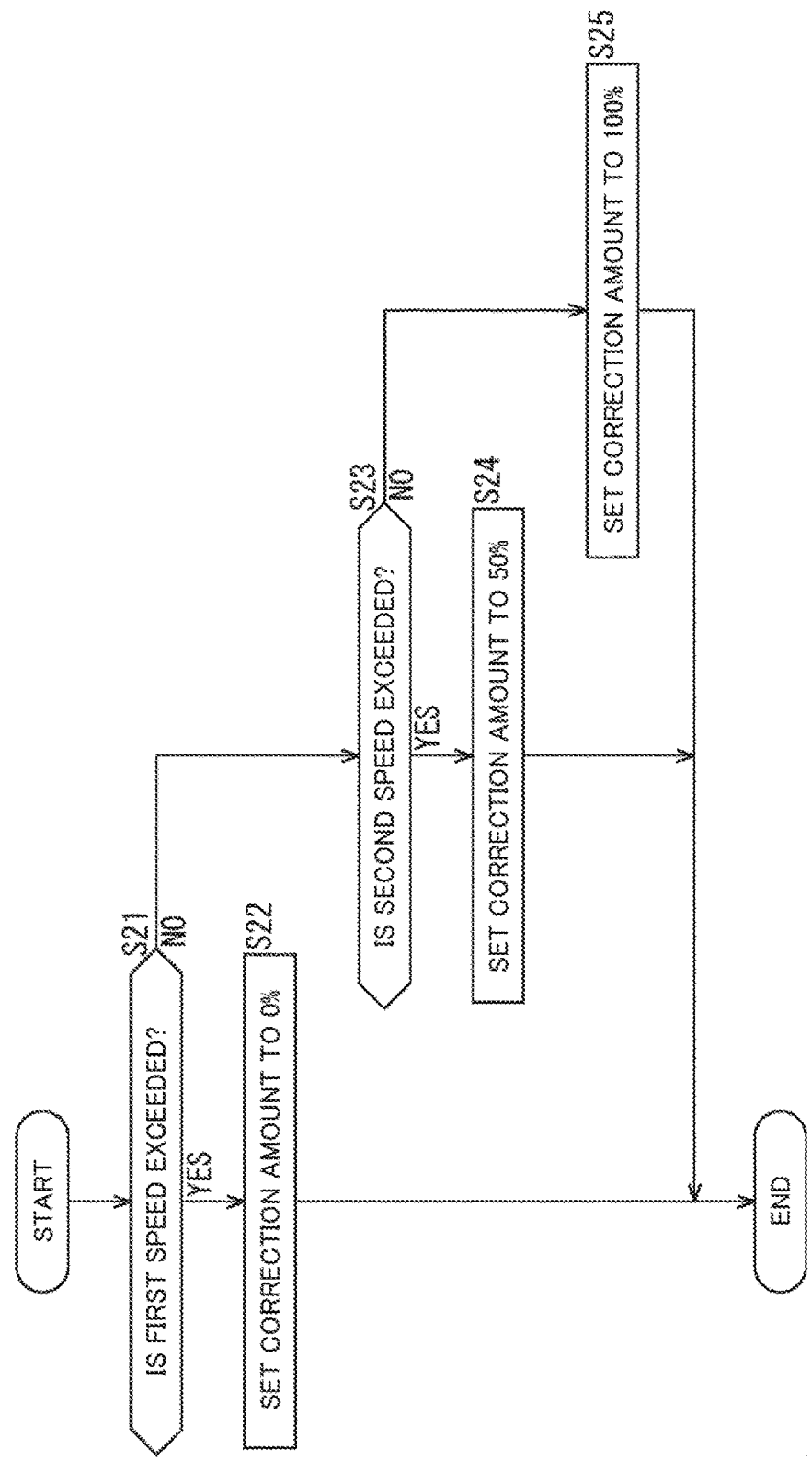
FIG. 8 is a flowchart illustrating a flow of operation of the correction control unit, according to a second embodiment.

FIG. 8 is a flowchart illustrating a flow of operation of the correction control unit 244, according to a second embodiment. The correction control unit 244 of the present embodiment sets a correction amount for the correction processing of the correction processing unit 241 according to the moving speed of a clipping area in a wide-angle image.

In step S21, the correction control unit 244 determines whether or not the moving speed of the clipping area exceeds a first speed.

If it is determined in step S21 that the moving speed of the clipping area exceeds the first speed, the processing proceeds to step S22, and then the correction control unit 244 sets the correction amount for the correction processing of the correction processing unit 241 to 0%.

On the other hand, if it is determined in step S21 that the moving speed of the clipping area does not exceed the first speed, the processing proceeds to step S23, and then the correction control unit 244 determines whether or not the moving speed of the clipping area exceeds a second speed. The second speed is a moving speed lower than the first speed.

If it is determined in step S23 that the moving speed of the clipping area exceeds the second speed, the processing proceeds to step S24, and then the correction control unit 244 sets the correction amount for the correction processing of the correction processing unit 241 to 50%. The correction amount to be set in step S24 is not limited to 50%, and may be another value between 0% and 100%.

On the other hand, if it is determined in step S23 that the moving speed of the clipping area does not exceed the second speed, the processing proceeds to step S24, and then the correction control unit 244 sets the correction amount for the correction processing of the correction processing unit 241 to 100%.

Figure 9:
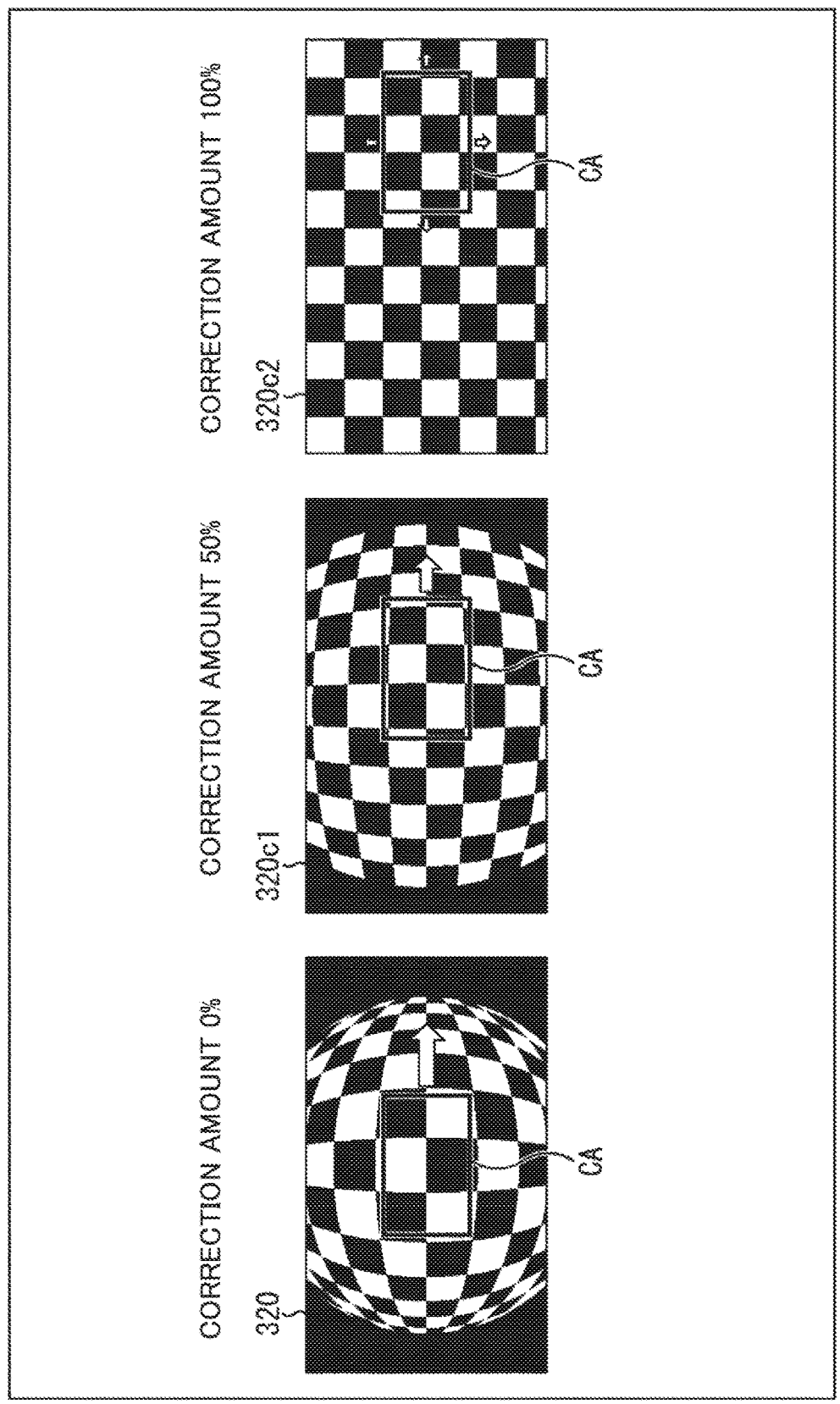
FIG. 9 is a diagram for explaining a correction amount according to a moving speed of a clipping area.

Clipping of a display image according to the present embodiment will now be described with reference to FIG. 9. In FIG. 9, the moving speed of the clipping area CA is indicated by the length and thickness of a block arrow.

As illustrated in the left part of FIG. 9, when the clipping area CA is moving relatively fast, a display image corresponding to the clipping area CA is clipped from a wide-angle image 320 obtained by the correction processing with a correction amount of 0% (as it is without having not been subjected to the correction processing).

As illustrated in the center of FIG. 9, when the clipping area CA is moving relatively slowly, a display image corresponding to the clipping area CA is clipped from a corrected wide-angle image 320*c*1 in which the correction processing with a correction amount of 50% has been performed on the wide-angle image 320.

As illustrated on the right side of FIG. 9, when the position of the clipping area CA is finely adjusted or is stopped, a display image corresponding to the clipping area CA is clipped from a corrected wide-angle image 320*c*2 in which the correction processing with a correction amount of 100% has been performed on the wide-angle image 320.

According to the above-described processing, when the surgeon moves the clipping area quickly, it is possible to determine a rough position where the clipping area is located in the wide-angle image from a display image clipped from the wide-angle image on which the correction processing has not been performed. In addition, when the surgeon moves the clipping area slowly, it is possible to determine where the clipping area is located in the wide-angle image from a display image clipped from the wide-angle image with less distortion, and then to determine an accurate position of the clipping area.

As described above, according to the present embodiment, it is possible to provide image display more helpful for the surgeon.

In the processing of FIG. 8, the correction amount for the correction processing is set stepwise according to whether or not the moving speed of the clipping area exceeds a predetermined threshold value (the first speed or the second speed). However, the correction amount for the correction processing may be changed according to the moving speed of the clipping area. For example, the correction amount for the correction processing may be changed linearly.

Figure 10:
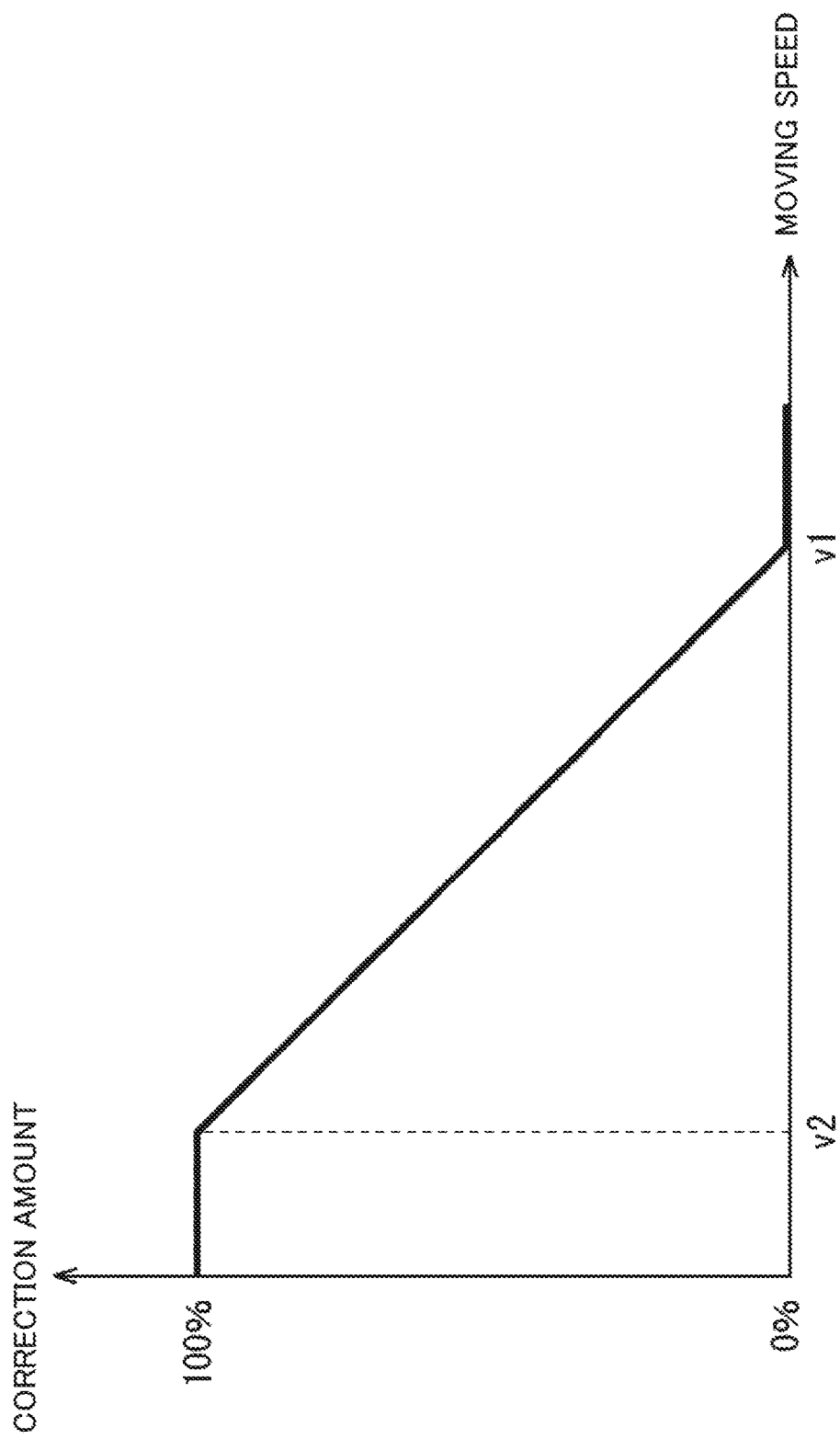
FIG. 10 is a diagram illustrating a relationship between the moving speed of a clipping area and the correction amount of a wide-angle image.

For example, as illustrated in FIG. 10, when the moving speed of the clipping area is lower than the first speed v1 and higher than the second speed v2, the correction amount for the correction processing may be increased (decreased) according to a decrease (increase) in the moving speed.

An embodiment has been described above in which the correction control unit 244 controls the correction processing of the correction processing unit 241 according to the moving state of the clipping area in the wide-angle image. The correction control unit 244 is not limited to such an embodiment, and may control the correction processing of the correction processing unit 241 according to the position of the clipping area in the wide-angle image.

As described above, the display control unit 243 can also control the display of a display image according to the relative state of the clipping area to the wide-angle image. Now, an embodiment will be described below in which the display control unit 243 controls the display of a display image according to a relative state of a clipping area to a wide-angle image.

<5. Third Embodiment (Display Control 1 According to Position of Clipping Area)>

Figure 11:
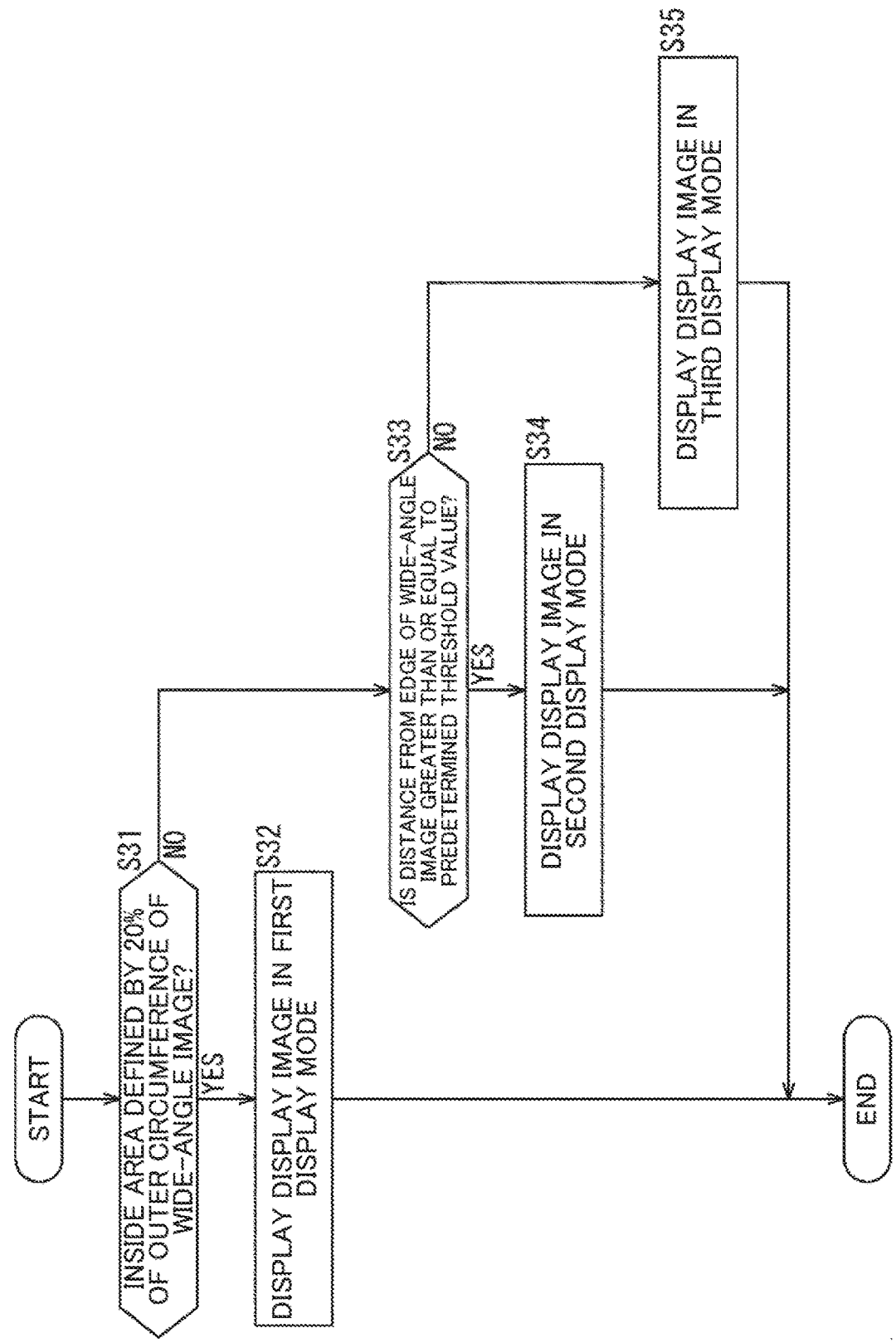
FIG. 11 is a flowchart illustrating a flow of operation of a display control unit, according to a third embodiment.

FIG. 11 is a flowchart illustrating a flow of operation of the display control unit 243, according to a third embodiment. The display control unit 243 according to the present embodiment changes the display mode for a display image according to the distance between a clipping area and an edge of the wide-angle image.

In step S31, the display control unit 243 determines whether or not the clipping area is inside an area defined by 20% of the outer circumference of the wide-angle image. Here, if the clipped area does not include the area defined by 20% of the outer circumference of the wide-angle image, it is determined that the clipped area is inside the area defined by 20% of the outer circumference of the wide-angle image.

If it is determined in step S31 that the clipping area is inside the area defined by 20% of the outer circumference of the wide-angle image, the processing proceeds to step S32, and then the display control unit 243 causes the display device 230 to display the corresponding display image in a first display mode. The first display mode is a display to inform that the clipping area is near the center of the wide-angle image.

On the other hand, if it is determined in step S31 that the clipping area is not inside the area defined by 20% of the outer circumference of the wide-angle image, the processing proceeds to step S33, and then the display control unit 243 determines whether or not the distance between the clipping area and an edge of the wide-angle image is greater than or equal to a predetermined threshold value.

If it is determined in step S33 that the distance between the clipping area and an edge of the wide-angle image is greater than or equal to the predetermined threshold value, the processing proceeds to step S34, and then the display control unit 243 causes the display device 230 to display the corresponding display image in a second display mode. The second display mode is a display to inform that the clipping area is approaching an edge of the wide-angle image.

On the other hand, if it is determined in step S33 that the distance between the clipping area and an edge of the wide-angle image is not greater than or equal to the predetermined threshold value, the processing proceeds to step S35, and then the display control unit 243 causes the display device 230 to display the corresponding display image in a third display mode. The third display mode is a display to inform that the clipping area is at a position very close to an edge of the wide-angle image.

Figure 12:
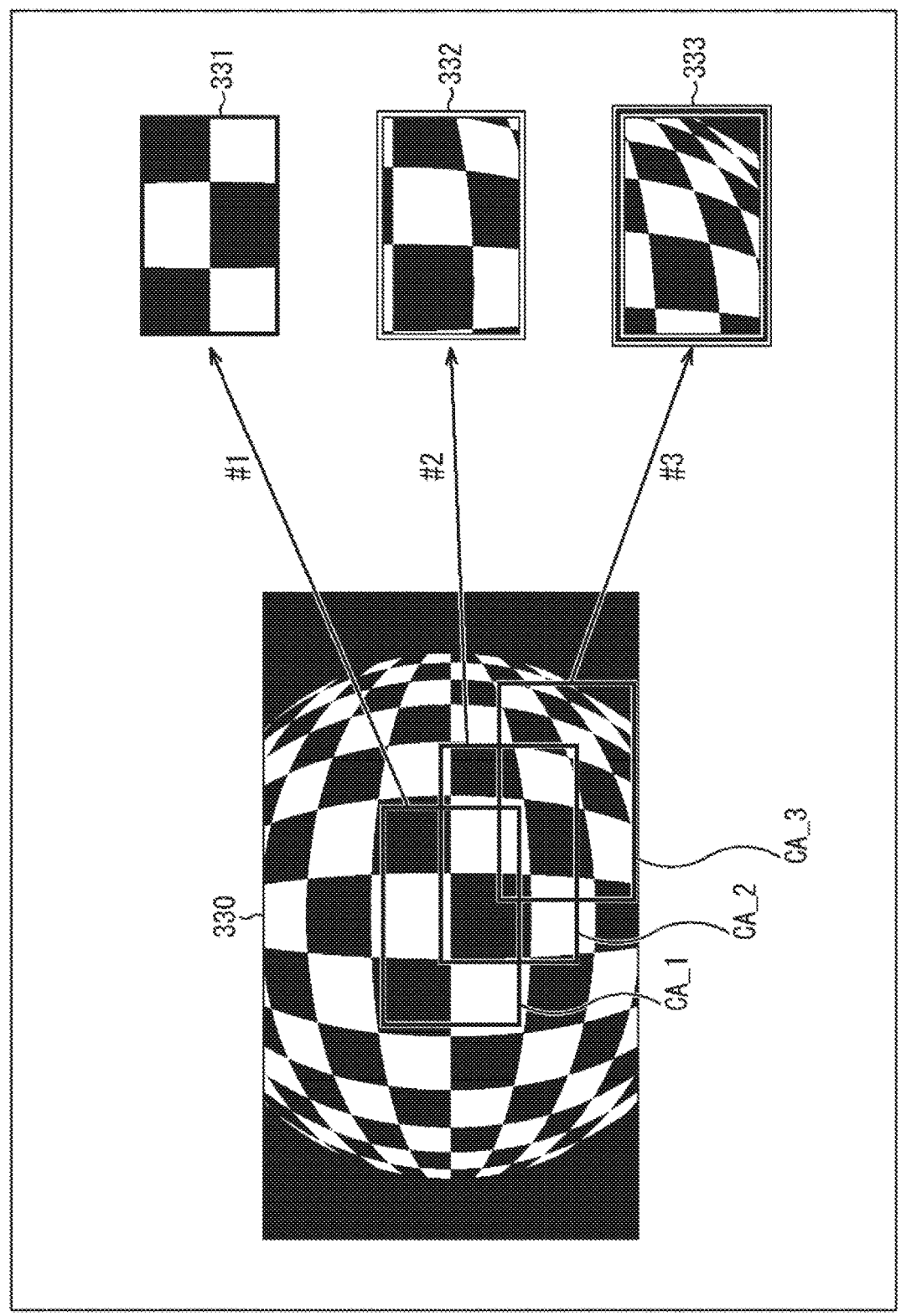
FIG. 12 is a diagram illustrating an example of a display image in a display mode according to the position of a clipping area.

A display image in a display mode according to the position of a clipping area according to the present embodiment will now be described with reference to FIGS. 12 and 13. In FIG. 12, it is assumed that the clipping area is moving in the wide-angle image. Accordingly, a display image is clipped from the wide-angle image on which the correction processing has not been performed.

As illustrated in FIG. 12, for example, when a clipping area CA_1 is substantially in the center of a wide-angle image 330 on which the correction processing has not been performed, a display image 331 with a predetermined frame added is displayed as indicated by arrow #1.

When a clipping area CA_2 is at a position which is off the center of the wide-angle image 330 and where it includes an area defined by 20% of the outer circumference of the wide-angle image 330, a display image 332 with a double-lined frame added is displayed as indicated by arrow #2.

When a clipping area CA_3 is at a position very close to an edge of the wide-angle image 330, a display image 333 with a triple-lined frame added is displayed as indicated by arrow #3.

Figure 13:
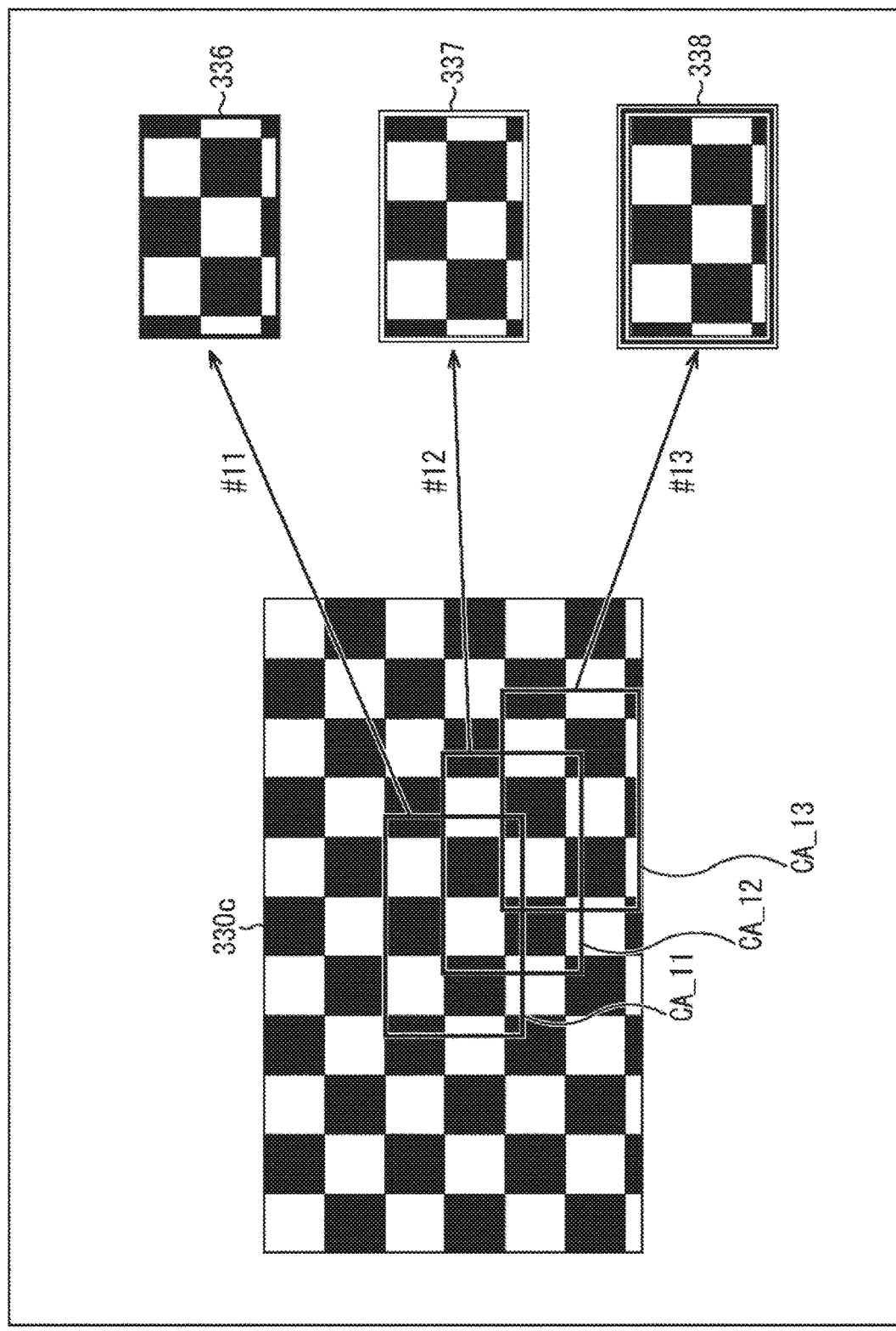
FIG. 13 is a diagram illustrating an example of a display image in a display mode according to the position of a clipping area.

In FIG. 13, it is assumed that the clipping area is stopped in the wide-angle image. Accordingly, a display image is clipped from the corrected wide-angle image in which the correction processing has been performed.

As illustrated in FIG. 13, for example, when a clipping area CA_11 is substantially in the center of a corrected wide-angle image 330c in which the correction processing has been performed, a display image 336 with a predetermined frame added is displayed as indicated by arrow #11.

When a clipping area CA_12 is at a position which is off the center of the wide-angle image 330c and where it includes an area defined by 20% of the outer circumference of the corrected wide-angle image 330c, a display image 337 with a double-lined frame added is displayed as indicated by arrow #12.

When a clipping area CA_13 is at a position very close to an edge of the corrected wide-angle image 330c, a display image 338 with a triple-lined frame added is displayed as indicated by arrow #13.

In FIGS. 12 and 13, the line type of the frame of the display image is changed according to the distance between the clipping area and an edge of the wide-angle image. However, the color and thickness of the frame of the display image may be changed.

For example, the frame to be added to the display image may be blue for the clipping area near the center of the wide-angle image, yellow for the clipping area at a position where it includes an area defined by 20% of the outer circumference of the wide-angle image, and red for the clipping area at a position very close to an edge of the wide-angle image.

Instead of or in addition to changing the display mode for the entire frame added to the display image, a part (side) of the frame added to the display image, which is near or in contact with an edge of the wide-angle image, may be changed according to the distance between the clipping area and the edge of the wide-angle image. In this case, the surgeon can move the clipping area while taking care of the direction in which an edge of the wide-angle image is located.

Instead of or in addition to changing the display mode for the frame of the display image, the display mode for the entire display image may be changed, such as by changing the brightness or resolution of the display image.

According to the above-described processing, it is possible to easily determine where the clipping area is located in the wide-angle image from the display mode for the corresponding display image.

For example, for a case where a display image is clipped from a corrected wide-angle image in which the distortion correction has been performed, or for a case where a subject of which distortion is difficult to recognize appears even in a wide-angle image on which the distortion correction has not been performed, it may not be possible to determine whether or not the clipping area is located near an edge of the wide-angle image.

For example, for a case where the image of a surgical site in an abdominal cavity is a wide-angle image, it is not easy to determine whether or not the clipping area is located near an edge of the wide-angle image from the shape of an organ or the like appearing in the display image.

Especially even for such a case, it is possible to easily determine where the clipping area is located in the wide-angle image from the display mode for the corresponding display image.

As described above, according to the present embodiment, it is possible to provide image display more helpful for the surgeon.

<6. Fourth Embodiment (Display Control 2 According to Position of Clipping Area)>

Figure 14:
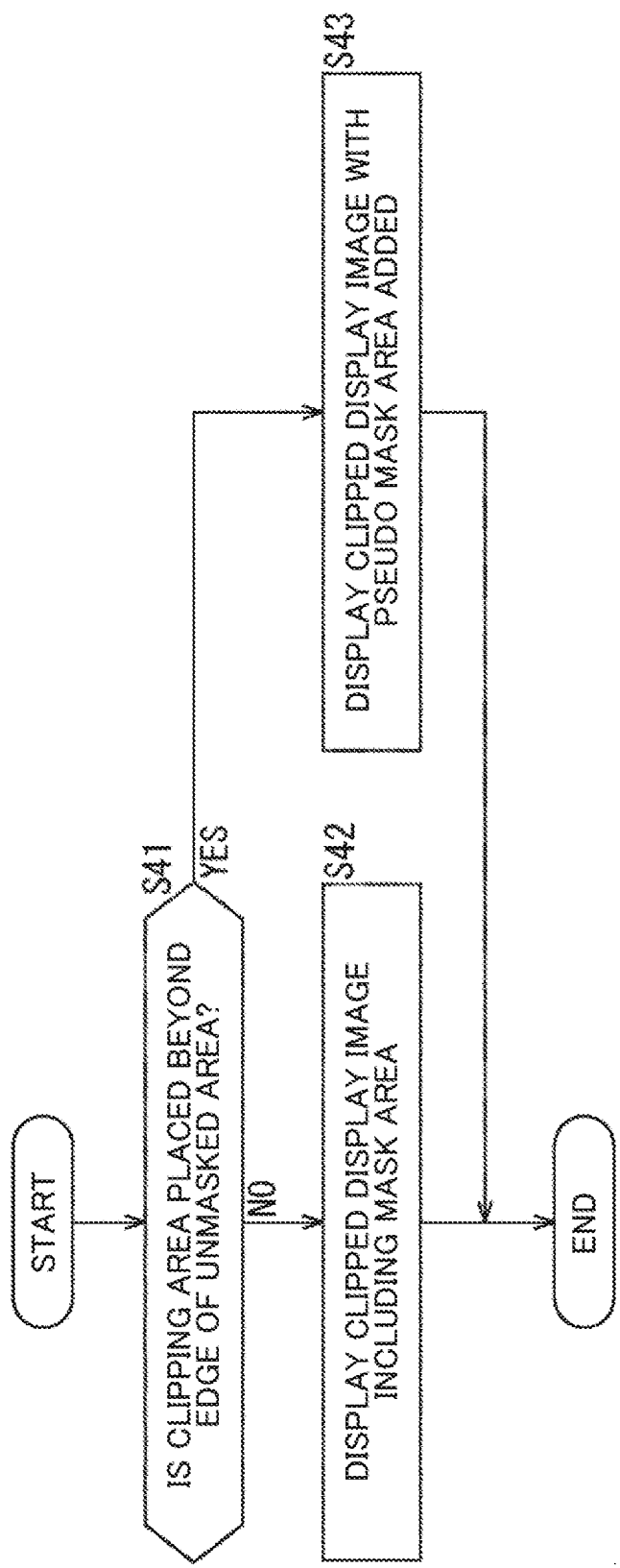
FIG. 14 is a flowchart illustrating a flow of operation of the display control unit, according to a fourth embodiment.

FIG. 14 is a flowchart illustrating a flow of operation of the display control unit 243, according to a fourth embodiment. In a state where the clipping area reaches an edge of the wide-angle image, if it cannot be determined from the clipped display image that the clipping area is located at the edge of the wide-angle image, the surgeon may try to move the clipping area further beyond the edge of the wide-angle image. Therefore, the display control unit 243 according to the present embodiment changes the display mode for the display image when there is a possibility that the surgeon will move the clipping area beyond an edge of the wide-angle image. As a user operation to move the clipping area as used herein, an operation to probably move the clipping area beyond an edge of the wide-angle image (note that the clipping area is not actually placed beyond an edge of the wide-angle image) is referred to as that the clipping area is placed beyond the edge of the wide-angle image.

In step S41, the display control unit 243 determines whether or not the clipping area is placed beyond an edge of an unmasked area in the wide-angle image.

Endoscopic images including the wide-angle images illustrated in the above-described embodiments include black shadows called "vignetting" in portions (left and right on the screen) where the imaging element (image size) is larger than the image circle of a lens. On the other hand, portions where the image size is smaller than the image circle (upper and lower portions on the screen) are not imaged and the subject is cut off. In addition, there is also a configuration in which a black image is synthesized as a mask image on the peripheral portion of an endoscope image according to the scope diameter of the endoscope. A black shadow or black image area in a wide-angle image is referred to as a mask area herein.

In other words, in step S41, it is determined whether or not the clipping area is placed beyond the upper or lower edge of the wide-angle image on the screen.

If it is determined in step S41 that the clipping area is not placed beyond an edge of an unmasked area in the wide-angle image, the processing proceeds to step S42, and then the display control unit 243 causes the display device 230 to display the clipped display image including a mask area.

On the other hand, if it is determined in step S41 that the clipping area is placed beyond an edge of an unmasked area in the wide-angle image, the processing proceeds to step S43, and then the display control unit 243 adds a pseudo mask area to the clipped display image and causes the display device 230 to display the resulting image.

Figure 15:
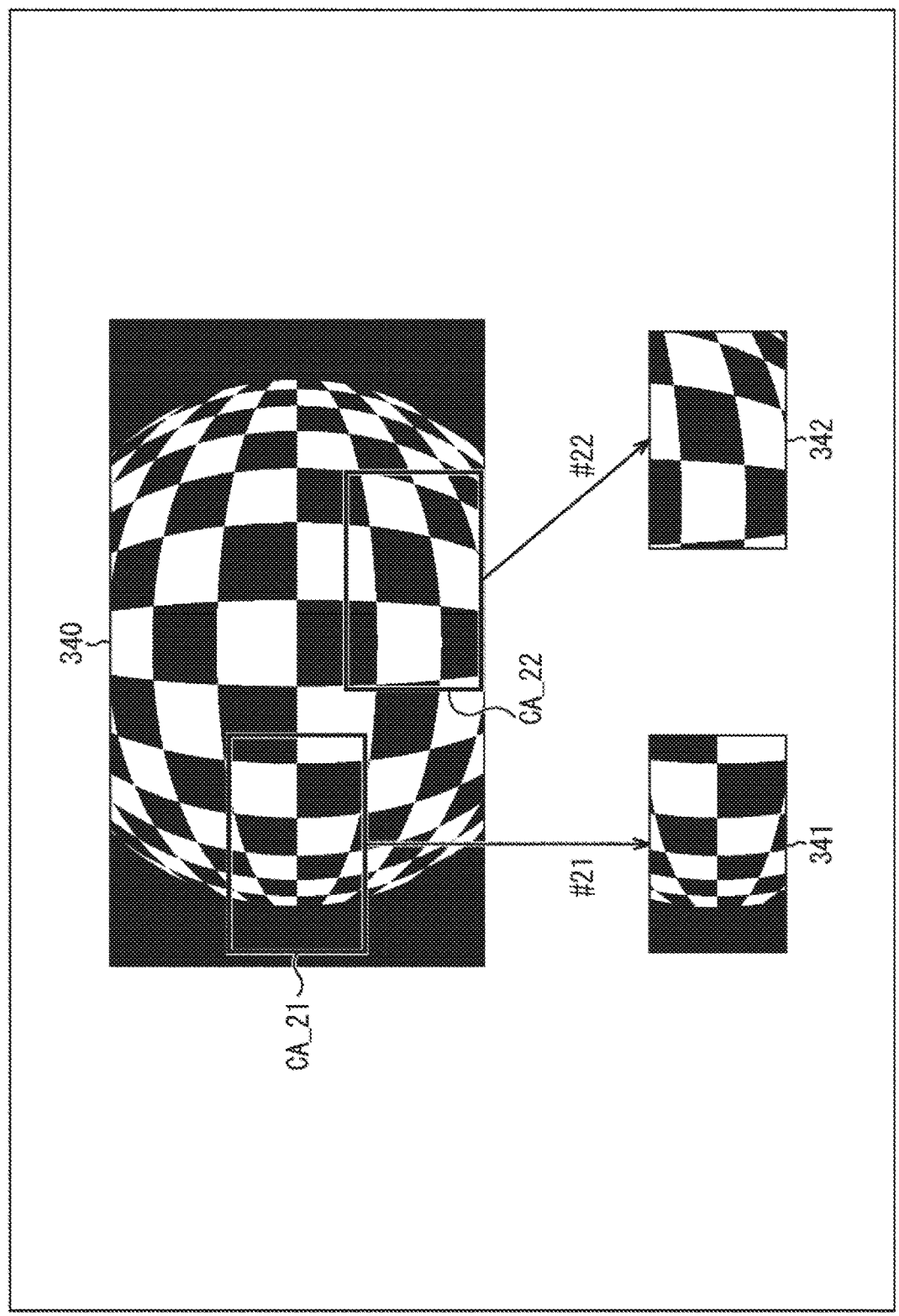
FIG. 15 is a diagram illustrating an example of a display image in a display mode according to the position of a clipping area.

FIG. 15 is a diagram illustrating a display image clipped from a wide-angle image by a conventional method.

As illustrated in FIG. 15, for example, when a clipping area CA_21 is in a left end of a wide-angle image 340 on which the correction processing has not been performed, a display image 341 including a mask area is displayed as indicated by arrow #21. In this case, the presence of the mask area makes it possible to easily determine that the clipping area is located at an edge of the wide-angle image.

On the other hand, when a clipping area CA_22 is in a lower end of the wide-angle image 340, a display image 342 not including a mask area is displayed as indicated by arrow #22. In this case, since there is no mask area, it is not possible to easily determine that the clipping area is located at an edge of the wide-angle image.

Figure 16:
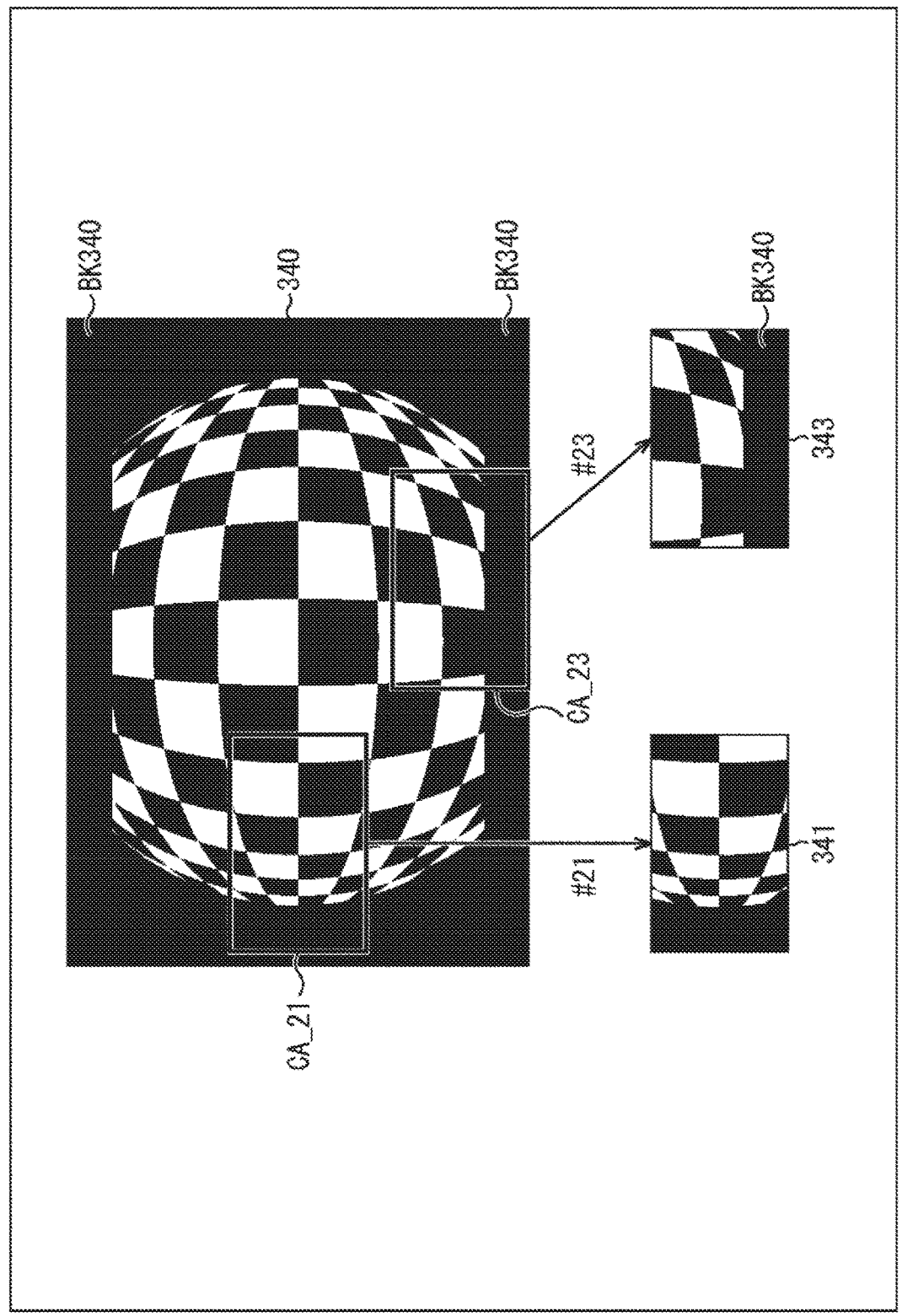
FIG. 16 is a diagram illustrating an example of a display image in a display mode according to the position of a clipping area.

FIG. 16 is a diagram illustrating a display image clipped from a wide-angle image by a method according to the present embodiment.

In the method according to the present embodiment, pseudo mask areas BK340, which are pseudo mask areas, are added in a wide-angle image 340 in upper and lower portions on the screen where the subject is cut off. A clipping area CA is movable on the wide-angle image 340 including the pseudo mask areas BK340.

In FIG. 16, a display image 341, corresponding to a clipping area CA_21, clipped from the wide-angle image 340 is the same as in the example of FIG. 15, and accordingly, the description thereof will be omitted.

When a clipping area CA_23 is in a lower end of the wide-angle image 340 including the pseudo mask areas BK340, a display image 343 including a pseudo mask area BK340 is displayed as indicated by arrow #23. As a result, even when the clipping area is approaching an edge of an unmasked area in the wide-angle image 340, the pseudo mask area BK340 makes it possible to easily determine that the clipping area is located at the edge of the wide-angle image.

Instead of adding the pseudo mask areas BK340 in upper and lower portions of the wide-angle image 340, when it is detected that the clipping area CA is placed beyond an upper or lower edge of the wide-angle image 340, a pseudo mask image may be synthesized and displayed in the upper or lower end of the display image.

As described above, according to the present embodiment, it is possible to provide image display more helpful for the surgeon.

<7. Another Configuration Example of Medical Observation System>

Figure 17:
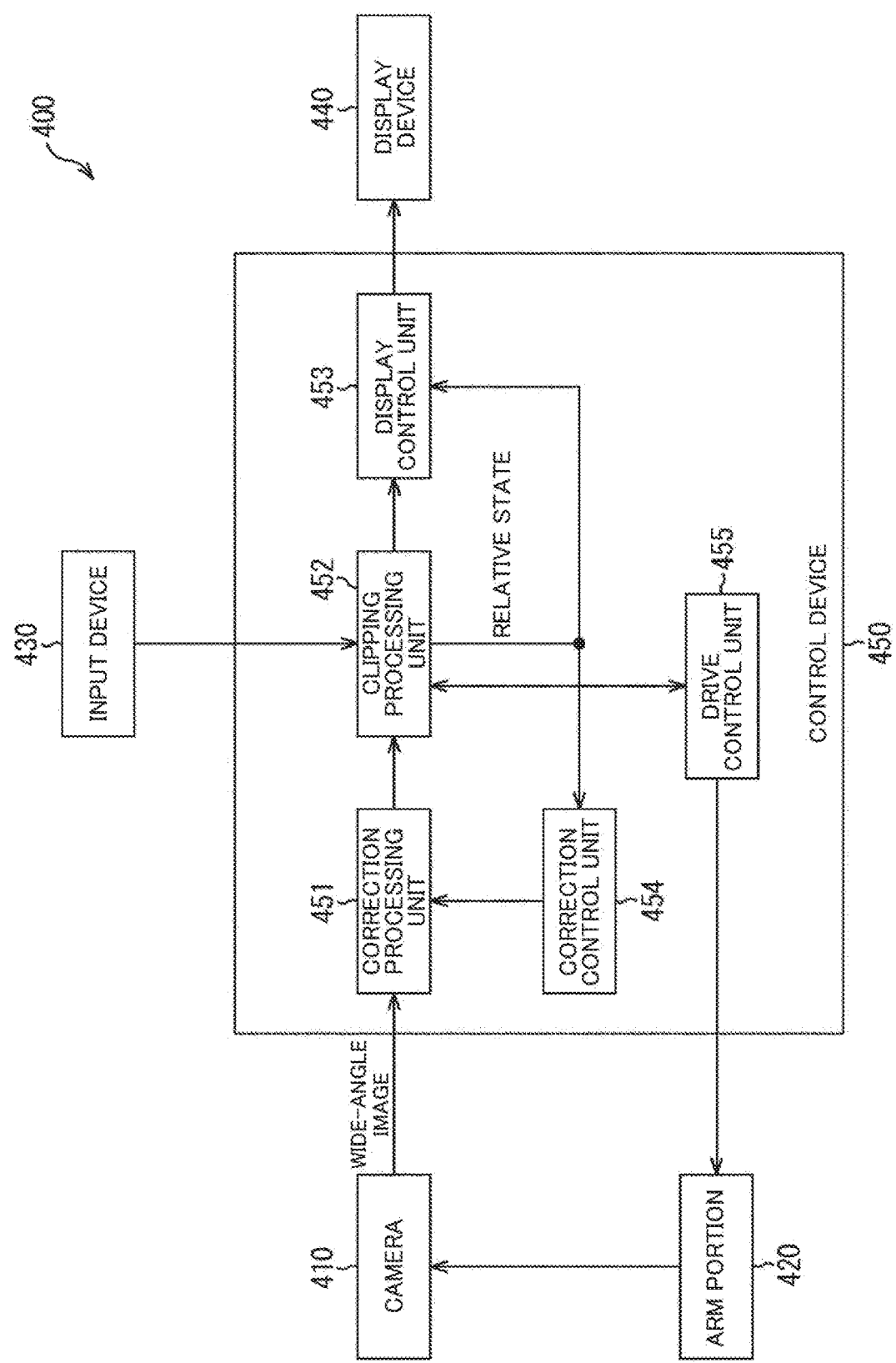
FIG. 17 is a block diagram illustrating another configuration example of a medical observation system according to an embodiment of the present disclosure.

FIG. 17 is a block diagram illustrating another configuration example of a medical observation system according to an embodiment of the present disclosure.

The medical observation system 400 illustrated in FIG. 17 includes a camera 410, an arm portion 420, an input device 430, a display device 440, and a control device 450.

The camera 410, the input device 430, and the display device 440 are the same as the camera 210, the input device 220, and the display device 230, respectively, in FIG. 3, and accordingly, the description thereof will be omitted.

The arm portion 420 corresponds to the arm portion 32 of the endoscopic surgery system 1 or the arm portion 112 of the microscopic surgery system 100, and supports the camera 410.

The control device 450 includes a correction processing unit 451, a clipping processing unit 452, a display control unit 453, a correction control unit 454, and a drive control unit 455.

The correction processing unit 451, the display control unit 453, and the correction control unit 454 are the same as the correction processing unit 241, the display control unit 243, and the correction control unit 244, respectively, in FIG. 3, and accordingly, the description thereof will be omitted.

The clipping processing unit 452 is the same as the clipping processing unit 242 in FIG. 3 in that it moves a clipping area on a wide-angle image in real time based on an operation signal from the input device 430. When the clipping area is placed beyond the range of the wide-angle image, the clipping processing unit 452 instructs the drive control unit 455 to drive the arm portion 420.

The drive control unit 455 controls the position and orientation of the camera 410 supported by the arm portion 420 by controlling the drive of the arm portion 420 based on instructions from the clipping processing unit 452. The drive control unit 455 also outputs information indicating the current position of the arm portion 420 within a drive range to the clipping processing unit 452 in real time.

Using the information from the drive control unit 455, the clipping processing unit 452 supplies to the display control unit 453 and the correction control unit 454 relative state information indicating a relative state of the clipping area to an allowable range for capturing a wide-angle image based on the drive range of the arm portion 420. This relative state includes the moving state (presence or absence of movement, moving speed, etc.) of the clipping area in the allowable range for capturing the wide-angle image, and the position of the clipping area in the allowable range for capturing the wide-angle image.

An embodiment will be described below in which the display control unit 453 controls the display of a display image according to a relative state of a clipping area to an allowable range for capturing a wide-angle image. In the following embodiments, the correction control unit 454 can also control the correction processing of the correction processing unit 241 according to the relative state of the clipping area to the allowable range for capturing the wide-angle image.

<8. Fifth Embodiment (Display Control 3 According to Position of Clipping Area)>

Figure 18:
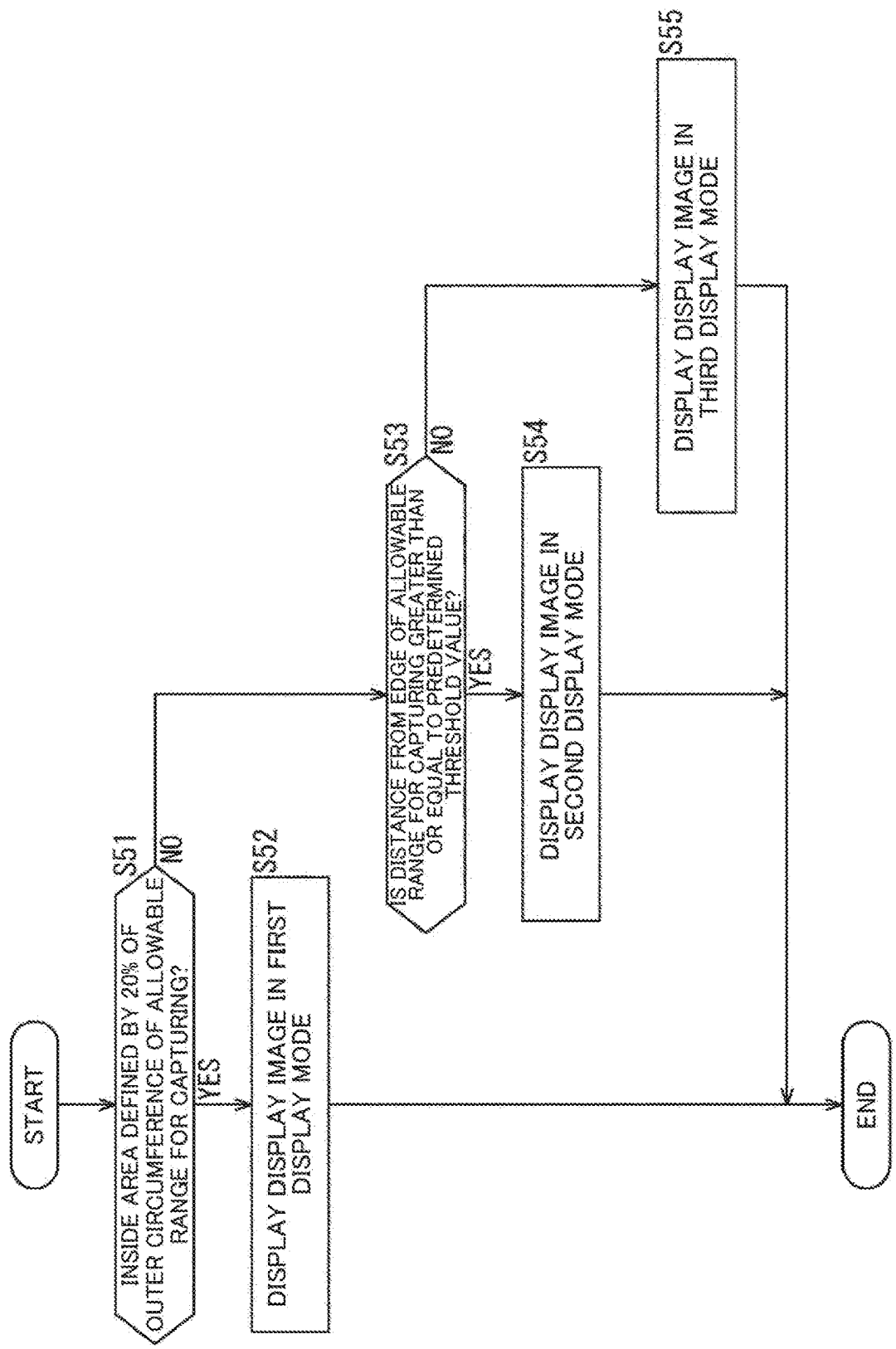
FIG. 18 is a flowchart illustrating a flow of operation of the display control unit, according to a fifth embodiment.

FIG. 18 is a flowchart illustrating a flow of operation of the display control unit 453, according to a fifth embodiment. The display control unit 453 according to the present embodiment changes the display mode for a display image according to the distance between a clipping area and an edge of an allowable range for capturing.

In step S51, the display control unit 453 determines whether or not the clipping area is inside an area defined by 20% of the outer circumference of the allowable range for capturing. Here, if the clipped area does not include the area defined by 20% of the outer circumference of the allowable range for capturing, it is determined that the clipped area is inside the area defined by 20% of the outer circumference of the allowable range for capturing.

If it is determined in step S51 that the clipping area is inside the area defined by 20% of the outer circumference of the allowable range for capturing, the processing proceeds to step S52, and then the display control unit 453 causes the display device 440 to display the corresponding display image in a first display mode.

On the other hand, if it is determined in step S51 that the clipping area is not inside the area defined by 20% of the outer circumference of the allowable range for capturing, the processing proceeds to step S53, and then the display control unit 243 determines whether or not the distance between the clipping area and an edge of the allowable range for capturing is greater than or equal to a predetermined threshold value.

If it is determined in step S53 that the distance between the clipping area and an edge of the allowable range for capturing is greater than or equal to the predetermined threshold value, the processing proceeds to step S54, and then the display control unit 453 causes the display device 440 to display the corresponding display image in a second display mode.

On the other hand, if it is determined in step S53 that the distance between the clipping area and an edge of the allowable range for capturing is not greater than or equal to the predetermined threshold value, the processing proceeds to step S54, and then the display control unit 453 causes the display device 440 to display the corresponding display image in a third display mode.

Figure 19:
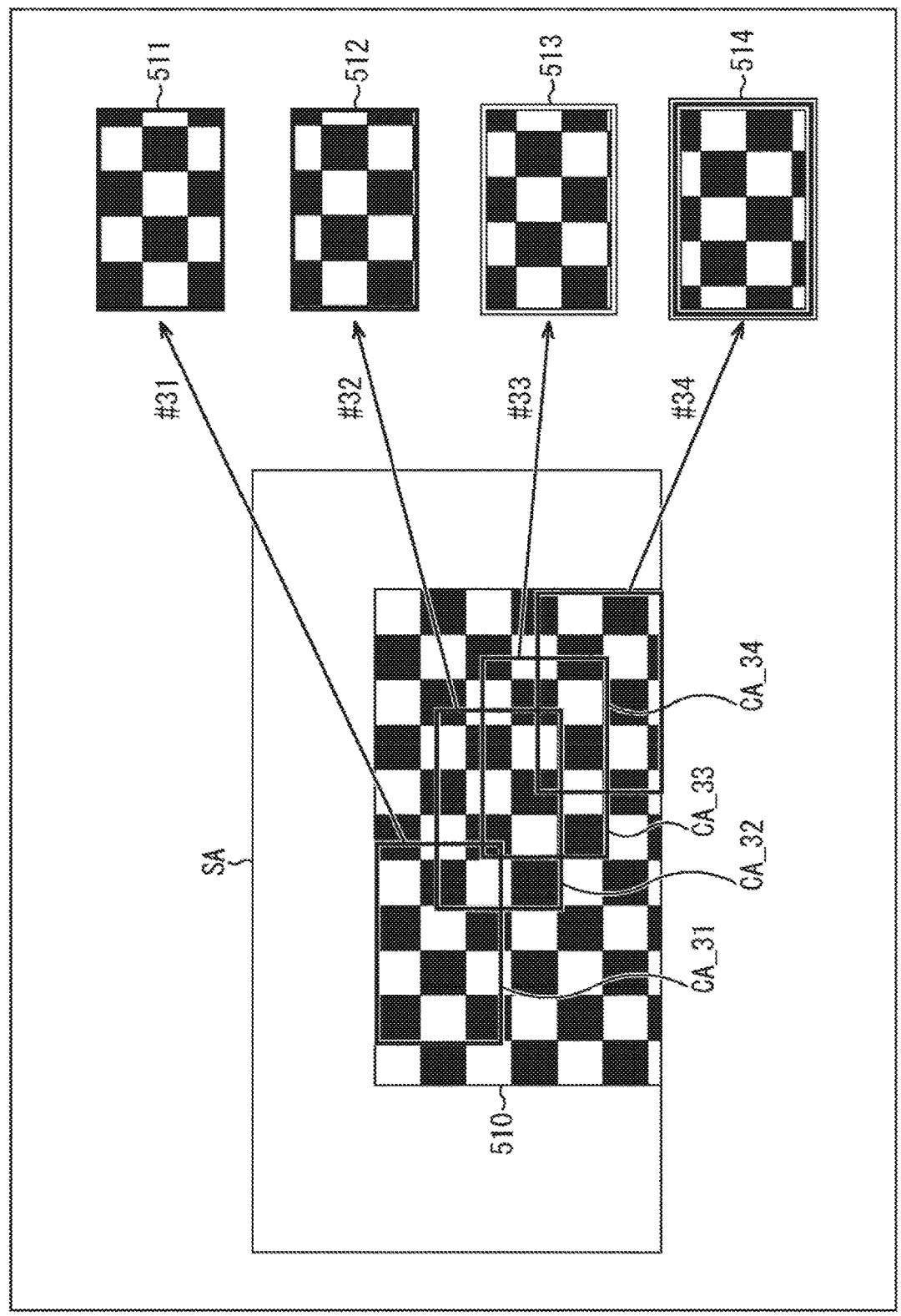
FIG. 19 is a diagram illustrating an example of a display image in a display mode according to the position of a clipping area.

A display image in a display mode according to the position of a clipping area according to the present embodiment will now be described with reference to FIG. 19. In FIG. 19, it is assumed that the clipping area is stopped in the wide-angle image. Accordingly, a display image is clipped from the corrected wide-angle image in which the correction processing has been performed. The clipping area may be moved in the wide-angle image, and the display image may be clipped from the wide-angle image on which the correction processing has not been performed.

In the example of FIG. 19, a wide-angle image 510 is an image of a subject captured in a lower end of an allowable range for capturing SA.

As illustrated in FIG. 19, for example, when a clipping area CA_31 is in an upper end of the wide-angle image 510 but substantially in the center of the allowable range for capturing SA, a display image 511 with a predetermined frame added is displayed as indicated by arrow #31.

When a clipping area CA_32 is at a position slightly off the center of the allowable range for capturing SA, a display image 512 with a predetermined frame added is displayed as indicated by arrow #32.

When a clipping area CA_33 is at a position which is off the center of the allowable range for capturing SA and where it includes an area defined by 20% of the outer circumference of the allowable range for capturing SA, a display image 513 with a double-lined frame added is displayed as indicated by arrow #33.

When a clipping area CA_34 is at a position very close to an edge of the allowable range for capturing SA, a display image 514 with a triple-lined frame added is displayed as indicated by arrow #34.

In FIG. 19, the line type of the frame of the display image is changed according to the distance between the clipping area and an edge of the allowable range for capturing. However, the color and thickness of the frame of the display image may be changed.

For example, the frame to be added to the display image is blue for the clipping area near the center of the allowable range for capturing, yellow for the clipping area at a position where it includes an area defined by 20% of the outer circumference of the allowable range for capturing, and red for the clipping area at a position very close to an edge of the allowable range for capturing.

Instead of or in addition to changing the display mode for the entire frame added to the display image, a part (side) of the frame added to the display image, which is near or in contact with an edge of the wide-angle image, may be changed according to the distance between the clipping area and the edge of the allowable range for capturing. In this case, the surgeon can move the clipping area while taking care of the direction in which an edge of the allowable range for capturing is located.

Instead of or in addition to changing the display mode for the frame of the display image, the display mode for the entire display image may be changed, such as by changing the brightness or resolution of the display image.

According to the above-described processing, it is possible to easily determine where the clipping area is located in the allowable range for capturing from the display mode for the corresponding display image.

In a case where the above-described third embodiment is applied to a configuration in which the position and orientation of the camera 410 can be controlled by driving the arm portion 420, even though a clipping area can be moved by driving the arm portion 420, the display mode for a display image changes according to the distance between the clipping area and an edge of the wide-angle image, so that it is not possible to accurately present the limits of movement of the clipping area.

On the other hand, according to the present embodiment, the display mode for a clipping area changes according to the distance between the clipping area and an edge of the allowable range for capturing, so that it is possible to more accurately present the limits of movement of the clipping area.

As described above, according to the present embodiment, it is possible to provide image display more helpful for the surgeon.

<9. Sixth Embodiment (Display Control 4 According to Position of Clipping Area)>

In the fifth embodiment described above, the display mode for a clipping area is changed according to only the distance between the clipping area and an edge of the allowable range for capturing. Therefore, for example, it is not possible to determine that the clipping area CA_31 is located at an edge of the wide-angle image 510, like the display image 511 in FIG. 19.

Figure 20:
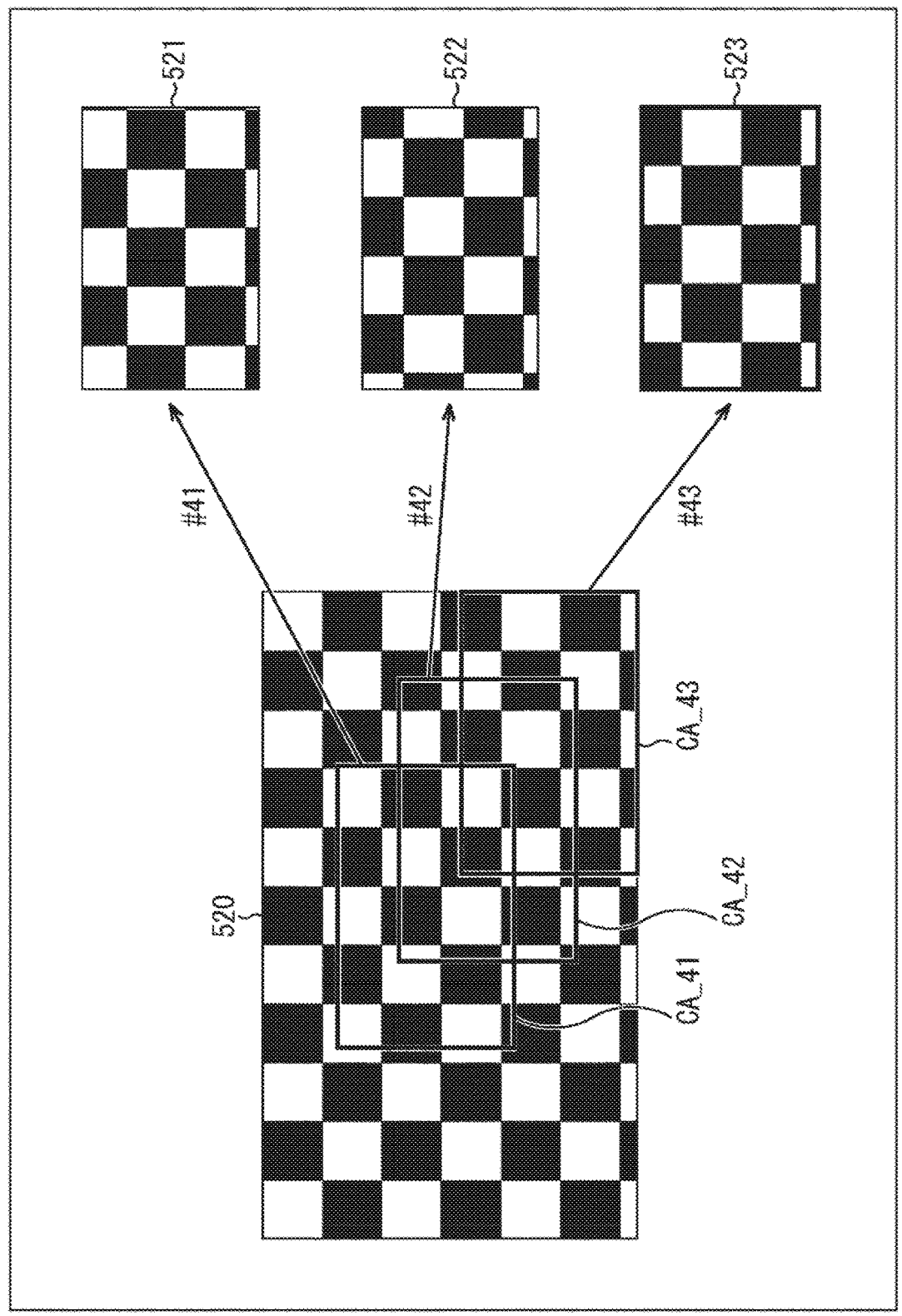
FIG. 20 is a diagram illustrating an example of a display image in a display mode according to the position of a clipping area.

Accordingly, as illustrated in FIG. 20, for example, when a clipping area CA_41 is substantially in the center of a wide-angle image 520, a display image 521 with no frame is displayed as indicated by arrow #41.

When a clipping area CA_42 is at a position off the center of the wide-angle image 520, a display image 332 with no frame is displayed as indicated by arrow #42.

When a clipping area CA_43 is at a position very close to an edge of the wide-angle image 520, a display image 523 with a predetermined frame added is displayed as indicated by arrow #43. At this time, the display mode for the frame of the display image 523 changes according to the distance between the clipping area and an edge of the allowable range for capturing, as will be described later.

As a result, it is possible to determine whether or not the clipping area is located at an edge of the wide-angle image, and where the clipping area is located in the allowable range for capturing.

In the example of FIG. 20, even when the clipping area CA_42 is at a position away from the edges of the wide-angle image 520, if the clipping area CA_42 includes an area defined by 20% of the outer circumference of the allowable range for capturing SA, a display image 532 to which a frame is added in the corresponding display mode is displayed.

Figure 21:
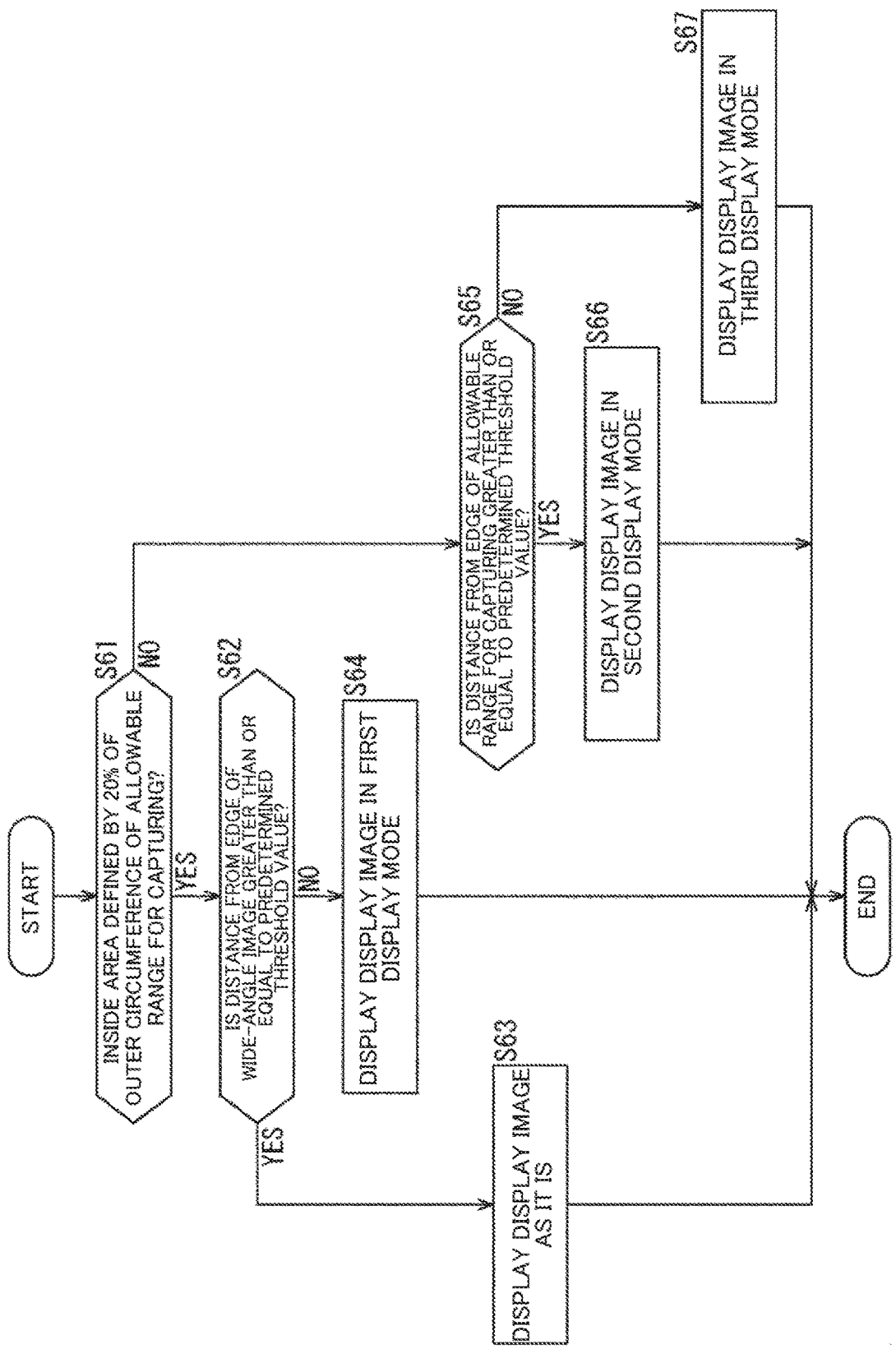
FIG. 21 is a flowchart illustrating a flow of operation of the display control unit, according to a sixth embodiment.

FIG. 21 is a flowchart illustrating a flow of operation of the display control unit 453, according to a sixth embodiment. The display control unit 453 according to the present embodiment changes the display mode for a display image according to the distance between a clipping area and an edge of the allowable range for capturing and the distance between the clipping area and an edge of the wide-angle image. Processing of steps S61 and S65 to S67 in the flowchart of FIG. 21 is the same as processing of steps S51 and S53 to S55 in the flowchart of FIG. 18, and accordingly, the description thereof will be omitted.

Accordingly, if it is determined in step S61 that the clipping area is inside the area defined by 20% of the outer circumference of the allowable range for capturing, the processing proceeds to step S62, and then the display control unit 453 determines whether or not the distance between the clipping area and an edge of the wide-angle image is greater than or equal to a predetermined threshold value.

If it is determined in step S62 that the distance between the clipping area and an edge of the wide-angle image is greater than or equal to the predetermined threshold value, the processing proceeds to step S63, and then the display control unit 453 causes the display device 440 to display the clipped display image as it is.

On the other hand, if it is determined in step S62 that the distance between the clipping area and an edge of the wide-angle image is not greater than or equal to the predetermined threshold value, the processing proceeds to step S64, and then the display control unit 453 causes the display device 440 to display the corresponding display image in a first display mode.

Figure 22:
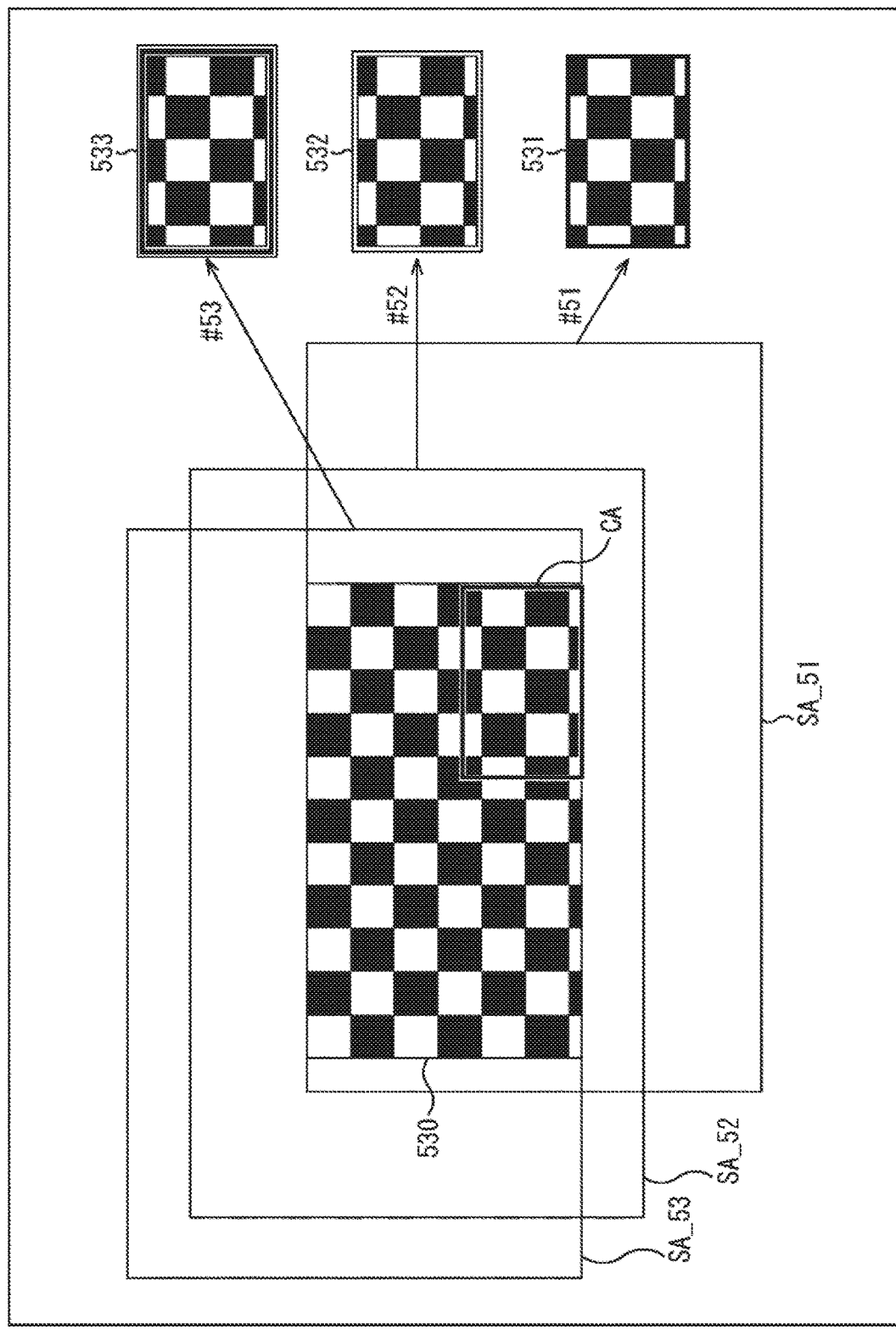
FIG. 22 is a diagram illustrating an example of a display image in a display mode according to the position of a clipping area.

A display image in a display mode according to the position of a clipping area according to the present embodiment will now be described with reference to FIG. 22. In FIG. 22, it is assumed that the clipping area is stopped in the wide-angle image. Accordingly, a display image is clipped from the corrected wide-angle image in which the correction processing has been performed. The clipping area may be moved in the wide-angle image, and the display image may be clipped from the wide-angle image on which the correction processing has not been performed.

As illustrated in FIG. 22, even when a clipping area CA is substantially in the center of an allowable range for capturing SA_51, if the clipping area CA is at a position very close to an edge of a wide-angle image 530, a display image 531 with a predetermined frame added is displayed as indicated by arrow #51.

When the clipping area CA is at a position where it includes an area defined by 20% of the outer circumference of an allowable range for capturing SA_52, a display image 532 with a double-lined frame added is displayed as indicated by arrow #52, regardless of the position of the clipping area CA in the wide-angle image 530.

When the clipping area CA is at a position very close to an end of an allowable range for capturing SA_53, a display image 533 with a triple-lined frame added is displayed as indicated by arrow #53, regardless of the position of the clipping area CA in the wide-angle image 530.

In FIG. 22, the line type of the frame of the display image is changed according to the distance between the clipping area and an edge of the allowable range for capturing, as in FIG. 19. However, the color and thickness of the frame of the display image, a part (side) of the frame added to the display image, which is near or in contact with an edge of the wide-angle image, or the display mode for the entire display image may be changed.

According to the above-described processing, it is possible to easily determine whether or not the clipping area is located very close to an edge of the wide-angle image from the display mode for the corresponding display image as well as where the clipping area is located in the allowable range for capturing.

As described above, according to the present embodiment, it is possible to provide image display more helpful for the surgeon.

Embodiments have been described above in which the display control unit 243 or the display control unit 453 controls the display of a display image according to the position of a clipping area in a wide-angle image or an allowable range for capturing. The display control unit 243 or the display control unit 453 is not limited to such embodiments, and may control the display of a display image (presence or absence of movement, moving speed, moving direction, etc.) of a clipping area in a wide-angle image or an allowable range for capturing.

For example, the display mode for a display image and/or the display mode for the frame of a display image may be changed according to the moving speed of the clipping area in the wide-angle image or the allowable range for capturing, in other words, the time to reach an edge of the wide-angle image or the allowable range for capturing.

<10. Hardware Configuration>

Finally, a hardware configuration example of a control device included in a medical observation system according to an embodiment of the present disclosure will be described with reference to FIG. 23.

Figure 23:
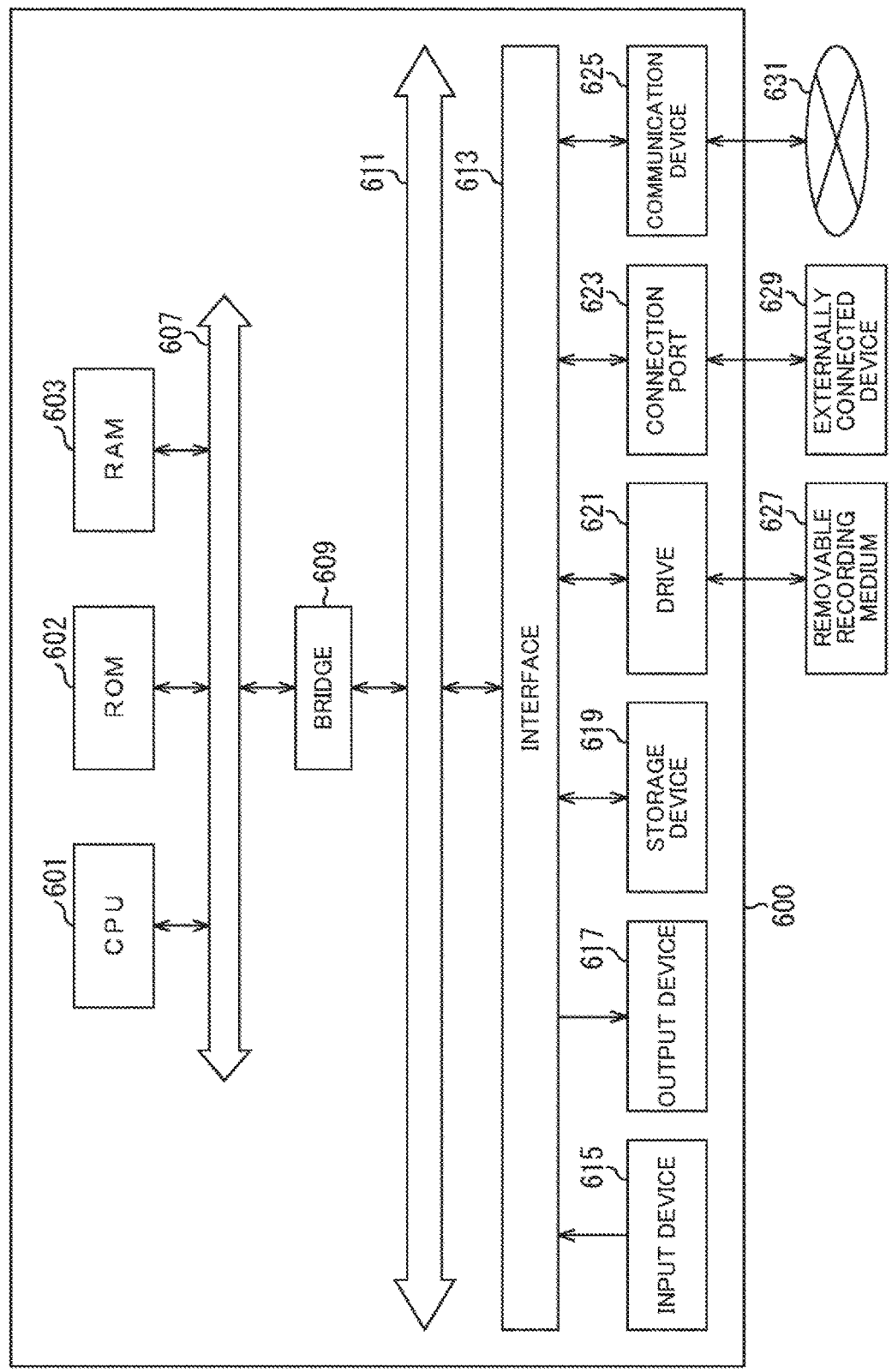
FIG. 23 is a block diagram illustrating a hardware configuration example of a control device.

As illustrated in FIG. 23, a control device 600 has a CPU 601, a ROM 603, and a RAM 605. The control device 600 also includes a host bus 607, a bridge 609, an external bus 611, an interface 613, an input device 615, an output device 617, and a storage device 619. The control device 600 may include a drive 621, a connection port 623, and a communication device 625.

The CPU 601 functions as an arithmetic processing device and a control device, and controls all or some of the operations in the control device 600 in accordance with various program recorded on the ROM 603, the RAM 605, the storage device 619, or a removable recording medium 627.

The ROM 603 stores programs, arithmetic parameters, and the like used by the CPU 601. The RAM 605 primarily stores programs used by the CPU 601, parameters which are appropriately changed during execution of the programs, and the like. These units are connected to each other by the host bus 607 including an internal bus such as a CPU bus. Each configuration of the control device 240 in FIG. 3 and the control device 450 in FIG. 17 is implemented by the CPU 601, for example.

The host bus 607 is connected to the external bus 611 such as a peripheral component interconnect/interface (PCI) bus via the bridge 609. The input device 615, the output device 617, the storage device 619, the drive 621, the connection port 623, and the communication device 625 are connected to the external bus 611 via the interface 613.

The input device 615 is, for example, operation means, such as a mouse, a keyboard, a touch panel, a button, a switch, a lever, and a pedal, which is operated by the surgeon. The input device 615 may be, for example, remote control means (a so-called remote controller) using infrared light or other radio waves or may be an externally connected device 629, such as a mobile phone or a PDA, which supports an operation on the control device 600.

The input device 615 includes an input control circuit or the like that generates an input signal based on information input by a surgeon using the operation means and outputs the input signal to the CPU 601.

The surgeon can operate the input device 615 to input various types of data to the control device 600 and to instruct the control device 600 to perform a processing operation.

The output device 617 is configured as a device that can notify the surgeon of acquired information visually or auditorily. Specifically, the output device 617 is configured as, for example, a display device such as a CRT display device, a liquid crystal display device, a plasma display device, an EL display device, and a lamp, a sound output device such as a speaker and a headphone, and/or a printer device.

The output device 617 outputs, for example, the results obtained through various types of processing performed by the control device 600. Specifically, the display device displays the results obtained through various types of processing performed by the control device 600 as text or images. On the other hand, the sound output device converts an audio signal formed from reproduced voice data, acoustic data, or the like into an analog signal and outputs the converted analog signal.

The storage device 619 is a data storage device configured as an example of a storage unit of the control device 600. The storage device 619 includes, for example, a magnetic storage device such as a hard disk drive (HDD), a semiconductor storage device, an optical storage device, or a magneto-optical storage device. The storage device 619 stores programs to be executed by the CPU 601 or various types of data.

The drive 621 is a recording medium reader/writer and is built in or externally attached to the control device 600. The drive 621 reads information recorded on the removable recording medium 627, such as a magnetic disk, an optical disc, a magneto-optical disc, or a semiconductor memory, which is mounted thereon, and outputs the information to the RAM 605. The drive 621 can also record information on the removable recording medium 627, such as a magnetic disk, an optical disc, a magneto-optical disc, or a semiconductor memory, which is mounted on.

The removable recording medium 627 is, for example, a DVD media, an HD-DVD medium, or a Blu-ray (registered trademark) medium. The removable recording medium 627 may be a compact flash (registered trademark), a flash memory, a secure digital (SD) memory card, or the like. The removable recording medium 627 may be, for example, an integrated circuit (IC) card on which a non-contact type IC chip is mounted, or an electronic device.

The connection port 623 is a port for directly connecting the externally connected device 629 to the control device 600. Examples of the connection port 623 include a universal serial bus (USB) port, an IEEE1394 port, and a small computer system interface (SCSI) port. Other examples of the connection port 623 include an RS-232C port, an optical audio terminal, and a high-definition multimedia interface (HDMI) (registered trademark) port. When the externally connected device 629 is connected to the connection port 623, the control device 600 directly acquires various types of data from the externally connected device 629 or supplies various types of data to the externally connected device 629.

The communication device 625 is, for example, a communication interface including a communication device or the like for connection to a communication network (network) 631. The communication device 625 is, for example, a communication card for a wired or wireless local area network (LAN), Bluetooth (registered trademark), or wireless USB (WUSB). The communication device 625 may be a router for optical communication, a router for asymmetric digital subscriber line (ADSL), or any of various types of communication modems.

The communication device 625 can transmit and receive a signal or the like to and from the Internet or another communication device in conformity with, for example, a predetermined protocol such as TCP/IP. The communication network 631 connected to the communication device 625 may be composed of a network connected in a wireless or wired manner and the like. The communication network 631 may be, for example, the Internet, a home LAN, or a communication network through which infrared communication, radio wave communication, or satellite communication is performed.

Each component of the control device 600 may be configured using a general-purpose member or may be configured using hardware specialized for the function of each component. Accordingly, the hardware configuration to be used can be changed as appropriate in accordance with a technical level when any one of the above-described embodiment is implemented.

A computer program can be created to implement each function of the control device 600 included in the medical observation system according to the above-described embodiments, and installed in a personal computer or the like. A computer-readable recording medium that stores the computer program can also be provided. Examples of the recording medium include a magnetic disk, an optical disc, a magneto-optical disc, and a flash memory. The computer program may be distributed via, for example, a network without using the recording medium.

In the present specification, a system means a set of a plurality of constituent elements (devices, modules (components), or the like) and all the constituent elements may be located or not located in the same casing. Accordingly, a plurality of devices accommodated in separate housings and connected via a network, and one device in which a plurality of modules are accommodated in one housing are both systems.

Note that embodiments of the present disclosure are not limited to the above-described embodiments and can be modified in various manners without departing from the scope and spirit of the present disclosure.

For example, the present disclosure may be configured as cloud computing in which a plurality of devices share and cooperatively process one function via a network.

In addition, each step described in the above flowchart can be executed by one device or executed in a shared manner by a plurality of devices.

Further, in a case where a plurality of kinds of processing are included in a single step, the plurality of kinds of processing included in the single step may be executed by one device or by a plurality of devices in a shared manner.

The present disclosure can be configured as follows.

(1) A medical observation system including:
 a correction processing unit that performs correction processing on a wide-angle image which is a captured image of a medical treatment target;
 a clipping processing unit that moves a clipping area for a display image clipped from the wide-angle image; and a correction control unit that controls the correction processing according to a relative state of the clipping area to the wide-angle image.

(2) The medical observation system according to (1), wherein the correction processing unit performs distortion correction on the wide-angle image.

(3) The medical observation system according to (1), wherein the correction processing unit performs luminance correction on the wide-angle image.

(4) The medical observation system according to any one of (1) to (3), wherein the relative state includes a moving state of the clipping area in the wide-angle image.

(5) The medical observation system according to (4), wherein
 the correction control unit
 disables the correction processing when the clipping area is moving, and
 enables the correction processing when the clipping area is stopped.

(6) The medical observation system according to (4), wherein the correction control unit sets a correction amount for the correction processing according to a moving speed of the clipping area.

(7) The medical observation system according to (6), wherein the correction control unit sets the correction amount stepwise according to whether the moving speed of the clipping area exceeds a predetermined threshold value.

(8) The medical observation system according to (6), wherein the correction control unit linearly changes the correction amount corresponding to the moving speed of the clipping area.

(9) The medical observation system according to any one of (1) to (8), further including a display control unit that controls display of the display image according to the relative state of the clipping area to the wide-angle image.

(10) The medical observation system according to (9), wherein the relative state includes at least one of a position and a moving state of the clipping area in the wide-angle image.

(11) The medical observation system according to (10), wherein the display control unit changes a display mode for the display image according to a distance between the clipping area and an edge of the wide-angle image.

(12) The medical observation system according to (11), wherein the display control unit changes a display mode for a frame of the display image according to the distance.

(13) The medical observation system according to (10), wherein the display control unit changes a display mode for the display image when the clipping area is placed beyond an edge of the wide-angle image.

(14) The medical observation system according to (13), wherein the display control unit displays the display image with a pseudo mask area added when the clipping area is placed beyond an edge of an unmasked area in the wide-angle image.

(15) The medical observation system according to any one of (1) to (14), further including a display control unit that controls display of the display image according to the relative state of the clipping area to an allowable range for the wide-angle image based on a driving range of an arm portion for supporting a camera that captures the wide-angle image.

(16) The medical observation system according to (15), wherein the relative state includes at least one of a position and a moving state of the clipping area in the allowable range for capturing.

(17) The medical observation system according to (16), wherein the display control unit changes a display mode for the display image according to a distance between the clipping area and an edge of the allowable range for capturing.

(18) The medical observation system according to (17), wherein the display control unit changes the display mode for the display image according to the distance between the clipping area and the edge of the allowable range for capturing and a distance between the clipping area and an edge of the wide-angle image.

(19) An image processing method performed by a medical observation system, the image processing method comprising:
 performing correction processing on a wide-angle image which is a captured image of a medical treatment target;
 moving a clipping area for a display image clipped from the wide-angle image; and controlling the correction processing according to a relative state of the clipping area to the wide-angle image.

(20) A program causing a computer to execute processing of:
performing correction processing on a wide-angle image which is a captured image of a medical treatment target;
moving a clipping area for a display image clipped from the wide-angle image; and
controlling the correction processing according to a relative state of the clipping area to the wide-angle image.

REFERENCE SIGNS LIST

1 Endoscopic surgery system
100 Microscopic surgery system
200 Medical observation system
210 Camera
220 Input device
230 Display device
240 Control device
241 Correction processing unit
242 Clipping processing unit
243 Display control unit
244 Correction control unit
400 Medical observation system
410 Camera
420 Arm portion
430 Input device
440 Display device
450 Control device
451 Correction processing unit
452 Clipping processing unit
453 Display control unit
454 Correction control unit
455 Drive control unit

The invention claimed is:

1. A medical observation system, comprising:
image processing circuitry configured to:
perform correction processing on a wide-angle image which is a captured image of a medical observation target;
move a clipping area for a display image clipped from the wide-angle image;
control the correction processing based on a relative state of the clipping area to the wide-angle image; and
control display of the display image according to the relative state of the clipping area to an allowable range for the wide-angle image, wherein the control of the display of the display image is based on a driving range of an arm portion for supporting a camera that captures the wide-angle image.

2. The medical observation system according to claim 1, wherein the image processing circuitry is further configured to perform distortion correction on the wide-angle image.

3. The medical observation system according to claim 1, wherein the image processing circuitry is further configured to perform luminance correction on the wide-angle image.

4. The medical observation system according to claim 1, wherein the relative state includes a moving state of the clipping area in the wide-angle image.

5. The medical observation system according to claim 4, wherein the image processing circuitry is further configured to:
disable the correction processing based on the movement of the clipping area; and
enable the correction processing based on stoppage of the movement of the clipping area.

6. The medical observation system according to claim 4, wherein the image processing circuitry is further configured to set a correction amount for the correction processing based on a moving speed of the clipping area.

7. The medical observation system according to claim 6, wherein the image processing circuitry is further configured to set the correction amount stepwise based on whether the moving speed of the clipping area exceeds a threshold value.

8. The medical observation system according to claim 6, wherein the image processing circuitry is further configured to linearly change the correction amount corresponding to the moving speed of the clipping area.

9. The medical observation system according to claim 1, wherein the relative state includes at least one of a position and a moving state of the clipping area in the wide-angle image.

10. The medical observation system according to claim 9, wherein the image processing circuitry is further configured to control change of a display mode for the display image based on a distance between the clipping area and an edge of the wide-angle image.

11. The medical observation system according to claim 10, wherein the image processing circuitry is further configured to control change of a display mode for a frame of the display image based on the distance.

12. The medical observation system according to claim 9, wherein the image processing circuitry is further configured to control change of a display mode for the display image based on placement of the clipping area beyond an edge of the wide-angle image.

13. The medical observation system according to claim 12, wherein the image processing circuitry is further configured to control display of the display image, with a pseudo mask area added, based on placement of the clipping area beyond an edge of an unmasked area in the wide-angle image.

14. The medical observation system according to claim 1, wherein the relative state includes at least one of a position and a moving state of the clipping area in the allowable range for capturing.

15. The medical observation system according to claim 14, wherein the image processing circuitry is further configured to control change of a display mode for the display image based on a distance between the clipping area and an edge of the allowable range for capture.

16. The medical observation system according to claim 15, wherein the image processing circuitry is further configured to control the change of the display mode for the display image based on the distance between the clipping area and the edge of the allowable range for capture and a distance between the clipping area and an edge of the wide-angle image.

17. An image processing method comprising:
performing correction processing on a wide-angle image which is a captured image of a medical observation target;
moving a clipping area for a display image clipped from the wide-angle image;
controlling the correction processing based on a relative state of the clipping area to the wide-angle image; and
controlling display of the display image according to the relative state of the clipping area to an allowable range for the wide-angle image, wherein the control of the display of the display image is based on a driving range of an arm portion for supporting a camera that captures the wide-angle image.

18. A non-transitory computer-readable medium having stored thereon computer-executable instructions that, when executed by a computer, causes the computer to execute operations, the operations comprising:
performing correction processing on a wide-angle image which is a captured image of a medical observation target;
moving a clipping area for a display image clipped from the wide-angle image;
controlling the correction processing based on a relative state of the clipping area to the wide-angle image; and
controlling display of the display image according to the relative state of the clipping area to an allowable range for the wide-angle image, wherein the control of the display of the display image is based on a driving range of an arm portion for supporting a camera that captures the wide-angle image.

* * * * *